US008871722B2

(12) United States Patent
Harding

(10) Patent No.: US 8,871,722 B2
(45) Date of Patent: Oct. 28, 2014

(54) PERHYDROLASE EPITOPES

(75) Inventor: Fiona A. Harding, Santa Clara, CA (US)

(73) Assignee: Danisco US Inc., Palo Alto, CA (US)

(*) Notice: Subject to any disclaimer, the term of this patent is extended or adjusted under 35 U.S.C. 154(b) by 1087 days.

(21) Appl. No.: 12/085,739

(22) PCT Filed: Dec. 4, 2006

(86) PCT No.: PCT/US2006/046203
§ 371 (c)(1),
(2), (4) Date: Feb. 18, 2009

(87) PCT Pub. No.: WO2007/067473
PCT Pub. Date: Jun. 14, 2007

(65) Prior Publication Data
US 2009/0258380 A1    Oct. 15, 2009

Related U.S. Application Data

(60) Provisional application No. 60/742,840, filed on Dec. 6, 2005.

(51) Int. Cl.
*A61K 38/16* (2006.01)
*C11D 3/386* (2006.01)
*G01N 33/50* (2006.01)
*C12N 9/18* (2006.01)
*C12N 9/16* (2006.01)

(52) U.S. Cl.
CPC .............. *C12N 9/18* (2013.01); *C11D 3/38636* (2013.01); *G01N 33/505* (2013.01); *C12N 9/16* (2013.01)
USPC ...................................................... 514/21.2

(58) Field of Classification Search
None
See application file for complete search history.

(56) References Cited

U.S. PATENT DOCUMENTS

| | | |
|---|---|---|
| 3,974,082 A | 8/1976 | Weyn |
| 4,400,237 A | 8/1983 | Kruger et al. |
| 4,760,025 A | 7/1988 | Estell et al. |
| 5,030,240 A | 7/1991 | Wiersema et al. |
| 5,108,457 A | 4/1992 | Poulouse et al. |
| 5,264,366 A | 11/1993 | Ferrari et al. |
| 5,296,616 A | 3/1994 | Namekawa et al. |
| RE34,606 E | 5/1994 | Estell et al. |
| 5,352,594 A | 10/1994 | Poulouse et al. |
| 5,601,750 A | 2/1997 | Domke et al. |
| 5,785,812 A | 7/1998 | Linsten et al. |
| 5,989,526 A | 11/1999 | Aaslyng et al. |
| 6,326,348 B1 | 12/2001 | Vinson et al. |
| 6,379,653 B1 | 4/2002 | Aaslyng et al. |
| 6,569,286 B1 | 5/2003 | Withenshaw et al. |
| 2002/0007516 A1 | 1/2002 | Wang |
| 2005/0158806 A1 | 7/2005 | Harding |

FOREIGN PATENT DOCUMENTS

| | | |
|---|---|---|
| EP | 1 255 888 | 9/2001 |
| WO | WO 92/10755 | 6/1992 |
| WO | WO 01/64993 | 9/2001 |
| WO | WO 03/002810 | 1/2003 |
| WO | WO 03/057713 | 7/2003 |
| WO | WO 03/072746 | 9/2003 |
| WO | WO 2004/078960 | 9/2004 |
| WO | WO 2005/056782 | 6/2005 |
| WO | WO 2005/062042 | 7/2005 |

OTHER PUBLICATIONS

Whisstock et al., 2003, Quart. Rev. Bioph. vol. 36: 307-340.*
Wang et al., 2001, J. Biol. Chem. vol. 276: 49213-49220.*
Altschul et al., "Basic Local Alignment Statistics," Methods in Enzymology, V. 266, pp. 460-480 (1993).
Altschul, Stephen F. et al., "Basic Local Alignment Search Tool," J. Mol. Biol. 215:403-410, 1990.
Baldry, "The bactericidal, fungicidal and sporicidal properties of hydrogen peroxide and peracetic acid," *J. of applied Bact.*, 1983, 54, 417-423.
Chang, et al. "High Frequency Transformation of *Bacillus subtilis* Protoplasts by Plasmid DNA," Mol. Gen. Genet. 168:111-115, 1979.
Devereux et al., "A Comprehensive set of sequence analysis programs for the VAX," Nucl. Acids Res., vol. 12, p. 387-395, 1984.
Feng et al., "Progressive Sequence Alignment as a Prerequisite to Correct Phylogenetic Tress" *J. Mol Evol.* vol. 25, pp. 351-360, 1987.
Ferrari, et al., in *Bacillus*, Harwood (ed.), Plenum Publishing Corporation, pp. 57-72, 1989.
Harding, F., "CD4+ T cell epitope identification: Applications to allergy," *Clinical and Experimental Allergy, Blackwell Scientific Publications, London, GB*, V. 33, N. 5, (2003) pp. 557-565.
Henikoff, Steven et al., "Amino acid substitution matrices from protein blocks," Proc. Natl. Acad. Sci. USA, 89:10915-10919, Nov. 1992.
Higgins et al., "Clustal: a package for performing multiple sequence alighment on a microcomputer," *Gene*, 73 (1988) 237-244.
Higgins et al., "Fast and sensitive multiple sequence alignments on microcomputer," CABIOS, vol. 5, 1989, p. 151-153.
Hofmann et al., "Bleaching Activators and the Mechanism of Bleaching Activation," *J. prakt Chem.*, 334 (1992) 293-297.

(Continued)

*Primary Examiner* — Amy Juedes
(74) *Attorney, Agent, or Firm* — Danisco US Inc.

(57) ABSTRACT

The present invention provides perhydrolase enzyme CD4+ T-cell epitopes, as well as variants that exhibit reduced immunogenic responses, as compared to the parental perhydrolase. The present invention further provides DNA molecules that encode perhydrolase variants, and host cells comprising DNA encoding perhydrolase variants, as well as methods for making perhydrolase enzymes less immunogenic. In addition, the present invention provides various compositions that comprise perhydrolase variants that are less immunogenic than the wild-type perhydrolase. In some specific embodiments, the present invention provides perhydrolase variants with reduced immunogenicity identified and/or characterized using the methods of the present invention. These enzymes find use in cleaning and other applications. In some preferred embodiments, the present invention finds particular use in applications involving cleaning, bleaching and disinfecting.

3 Claims, No Drawings

(56) References Cited

OTHER PUBLICATIONS

Karlin et al., "Applications and statistics for multiple high-scoring segments in molecular sequences," Proc. Natl. Acad. Sci. USA, vol. 90, pp. 5873-5877, Jun. 1993.

Maeji et al., "Multi-pin peptide synthesis strategy for T cell determinant analysis," *J. of Immun. Methods*, 134 (1990) 23-33 Elsevier.

Mori, et al., "HLA Gene and Haplotype Frequencies in the North American Population" *Transplantation*, V. 647) (1997) pp. 1017-1027.

Needleman et al., "A General Method Applicable to the Search for Similarities in the Amino Acid Sequence of Two Proteins," *J. Mol. Biol.*, vol. 48, pp. 443-453, 1970.

Pearson et al., "Improved tools for biological sequence comparison," Proc. Natl. Acad. Sci. USA, vol. 85, pp. 2444-2448, Apr. 1988.

Smith et al., "Comparison of Biosequences," Adv. In App. Math. vol. 2, pp. 482-489, 1981.

Smith, Michael et al., "Protoplast Transformation in Coryneform Bacteria and Introduction of an α-Amylase Gene from *Bacillus amyloliquefaciens* into *Brevibacterium lactofermentum*," *Applied and Environmental Microbiology*, vol. 51, No. 3, pp. 634-639, Mar. 1986.

Stickler et al., "An in vitro human cell-based assay to rank the relative immunogenicity of proteins," *Toxicological Sciences, Academic Press, San Diego, FL., US*, V. 77, N. 2, (2004) pp. 280-289.

Stickler et al., "CD4+ T cell epitope determination using unexposed human donor peripheral blood mononuclear cells," *J. of Immunotherapy, Lippincott Williams & Wilkins, Hagerstown, MD, US*, V. 23, N. 6, (2000) pp. 654-660.

Stickler et al., "A Human dendritic cell-based Method to Identify CD4+ T-Cell epitopes in potential protein allergens," *Environmental Health Perspectives*, V. 111, N. 2, (2003) pp. 251-254.

Schweigert et al., "Occupational asthma and allergy associated with the use of enzymes in the detergent industry—a review of the epidemiology, toxicology and methods of prevention," *Clinical and Experimental Allergy: J. of the British Society for Allergy and Clinical Immunology*, (2000) V. 30, N. 1, pp. 1511-1518.

Stickler, M., et al. "Human population-based identification of CD4+ T-cell peptide epitope determinants." *Journal of Immunological Methods* 281(1-2): 95-108, 2003.

International Search Report and the Written Opinion of the International Searching Authority for International Patent Application No. PCT/US2006/046203 dated Jul. 23, 2007.

* cited by examiner

SEQUENCE LISTING

```
<160> NUMBER OF SEQ ID NOS: 71

<210> SEQ ID NO 1
<211> LENGTH: 651
<212> TYPE: DNA
<213> ORGANISM: Mycobacterium smegmatis

<400> SEQUENCE: 1
atggccaagc gaattctgtg tttcggtgat tccctgacct ggggctgggt ccccgtcgaa     60
gacggggcac ccaccgagcg gttcgccccc gacgtgcgct ggaccggtgt gctggcccag    120
cagctcggag cggacttcga ggtgatcgag gagggactga gcgcgcgcac caccaacatc    180
gacgacccca ccgatccgcg gctcaacggc gcgagctacc tgccgtcgtg cctcgcgacg    240
cacctgccgc tcgacctggt gatcatcatg ctgggcacca acgacaccaa ggcctacttc    300
cggcgcaccc gctcgacat cgcgctgggc atgtcggtgc tcgtcacgca ggtgctcacc     360
agcgcgggcg gcgtcggcac cacgtacccg gcacccaagg tgctggtggt ctcgccgcca    420
ccgctggcgc ccatgccgca ccctggttc cagttgatct cgagggcgg cgagcagaag      480 accactgagc tcgcccgcgt gtacagcgcg ctcgcgtcgt tcatgaaggt gccgttcttc    540
gacgcgggtt cggtgatcag caccgacggc gtcgacggaa tccacttcac cgaggccaac    600
aatcgcgatc tcggggtggc cctcgcggaa caggtgcgga gcctgctgta a             651

<210> SEQ ID NO 2
<211> LENGTH: 216
<212> TYPE: PRT
<213> ORGANISM: Mycobacterium smegmatis

<400> SEQUENCE: 2

Met Ala Lys Arg Ile Leu Cys Phe Gly Asp Ser Leu Thr Trp Gly Trp
1               5                  10                  15

Val Pro Val Glu Asp Gly Ala Pro Thr Glu Arg Phe Ala Pro Asp Val
                20                  25                  30

Arg Trp Thr Gly Val Leu Ala Gln Gln Leu Gly Ala Asp Phe Glu Val
            35                  40                  45

Ile Glu Glu Gly Leu Ser Ala Arg Thr Thr Asn Ile Asp Asp Pro Thr
        50                  55                  60

Asp Pro Arg Leu Asn Gly Ala Ser Tyr Leu Pro Ser Cys Leu Ala Thr
65                  70                  75                  80

His Leu Pro Leu Asp Leu Val Ile Met Leu Gly Thr Asn Asp Thr
                85                  90                  95

Lys Ala Tyr Phe Arg Arg Thr Pro Leu Asp Ile Ala Leu Gly Met Ser
                100                 105                 110

Val Leu Val Thr Gln Val Leu Thr Ser Ala Gly Gly Val Gly Thr Thr
            115                 120                 125

Tyr Pro Ala Pro Lys Val Leu Val Val Ser Pro Pro Leu Ala Pro
        130                 135                 140

Met Pro His Pro Trp Phe Gln Leu Ile Phe Glu Gly Gly Glu Gln Lys
```

```
                145                 150                 155                 160
Thr Thr Glu Leu Ala Arg Val Tyr Ser Ala Leu Ala Ser Phe Met Lys
                165                 170                 175

Val Pro Phe Phe Asp Ala Gly Ser Val Ile Ser Thr Asp Gly Val Asp
                180                 185                 190

Gly Ile His Phe Thr Glu Ala Asn Asn Arg Asp Leu Gly Val Ala Leu
            195                 200                 205

Ala Glu Gln Val Arg Ser Leu Leu
        210                 215

<210> SEQ ID NO 3
<211> LENGTH: 15
<212> TYPE: PRT
<213> ORGANISM: Mycobacterium smegmatis

<400> SEQUENCE: 3

Met Ala Lys Arg Ile Leu Cys Phe Gly Asp Ser Leu Thr Trp Gly
1               5                   10                  15

<210> SEQ ID NO 4
<211> LENGTH: 15
<212> TYPE: PRT
<213> ORGANISM: Mycobacterium smegmatis

<400> SEQUENCE: 4

Arg Ile Leu Cys Phe Gly Asp Ser Leu Thr Trp Gly Trp Val Pro
1               5                   10                  15

<210> SEQ ID NO 5
<211> LENGTH: 15
<212> TYPE: PRT
<213> ORGANISM: Mycobacterium smegmatis

<400> SEQUENCE: 5

Cys Phe Gly Asp Ser Leu Thr Trp Gly Trp Val Pro Val Glu Asp
1               5                   10                  15

<210> SEQ ID NO 6
<211> LENGTH: 15
<212> TYPE: PRT
<213> ORGANISM: Mycobacterium smegmatis

<400> SEQUENCE: 6

Asp Ser Leu Thr Trp Gly Trp Val Pro Val Glu Asp Gly Ala Pro
1               5                   10                  15

<210> SEQ ID NO 7
<211> LENGTH: 15
<212> TYPE: PRT
<213> ORGANISM: Mycobacterium smegmatis

<400> SEQUENCE: 7

Thr Trp Gly Trp Val Pro Val Glu Asp Gly Ala Pro Thr Glu Arg
1               5                   10                  15

<210> SEQ ID NO 8
<211> LENGTH: 15
<212> TYPE: PRT
<213> ORGANISM: Mycobacterium smegmatis

<400> SEQUENCE: 8

Trp Val Pro Val Glu Asp Gly Ala Pro Thr Glu Arg Phe Ala Pro
1               5                   10                  15
```

<210> SEQ ID NO 9
<211> LENGTH: 15
<212> TYPE: PRT
<213> ORGANISM: Mycobacterium smegmatis

<400> SEQUENCE: 9

Val Glu Asp Gly Ala Pro Thr Glu Arg Phe Ala Pro Asp Val Arg
1               5                   10                  15

<210> SEQ ID NO 10
<211> LENGTH: 15
<212> TYPE: PRT
<213> ORGANISM: Mycobacterium smegmatis

<400> SEQUENCE: 10

Gly Ala Pro Thr Glu Arg Phe Ala Pro Asp Val Arg Trp Thr Gly
1               5                   10                  15

<210> SEQ ID NO 11
<211> LENGTH: 15
<212> TYPE: PRT
<213> ORGANISM: Mycobacterium smegmatis

<400> SEQUENCE: 11

Thr Glu Arg Phe Ala Pro Asp Val Arg Trp Thr Gly Val Leu Ala
1               5                   10                  15

<210> SEQ ID NO 12
<211> LENGTH: 15
<212> TYPE: PRT
<213> ORGANISM: Mycobacterium smegmatis

<400> SEQUENCE: 12

Phe Ala Pro Asp Val Arg Trp Thr Gly Val Leu Ala Gln Gln Leu
1               5                   10                  15

<210> SEQ ID NO 13
<211> LENGTH: 15
<212> TYPE: PRT
<213> ORGANISM: Mycobacterium smegmatis

<400> SEQUENCE: 13

Asp Val Arg Trp Thr Gly Val Leu Ala Gln Gln Leu Gly Ala Asp
1               5                   10                  15

<210> SEQ ID NO 14
<211> LENGTH: 15
<212> TYPE: PRT
<213> ORGANISM: Mycobacterium smegmatis

<400> SEQUENCE: 14

Trp Thr Gly Val Leu Ala Gln Gln Leu Gly Ala Asp Phe Glu Val
1               5                   10                  15

<210> SEQ ID NO 15
<211> LENGTH: 15
<212> TYPE: PRT
<213> ORGANISM: Mycobacterium smegmatis

<400> SEQUENCE: 15

Val Leu Ala Gln Gln Leu Gly Ala Asp Phe Glu Val Ile Glu Glu
1               5                   10                  15

```
<210> SEQ ID NO 16
<211> LENGTH: 15
<212> TYPE: PRT
<213> ORGANISM: Mycobacterium smegmatis

<400> SEQUENCE: 16

Gln Gln Leu Gly Ala Asp Phe Glu Val Ile Glu Glu Gly Leu Ser
1               5                   10                  15

<210> SEQ ID NO 17
<211> LENGTH: 15
<212> TYPE: PRT
<213> ORGANISM: Mycobacterium smegmatis

<400> SEQUENCE: 17

Gly Ala Asp Phe Glu Val Ile Glu Glu Gly Leu Ser Ala Arg Thr
1               5                   10                  15

<210> SEQ ID NO 18
<211> LENGTH: 15
<212> TYPE: PRT
<213> ORGANISM: Mycobacterium smegmatis

<400> SEQUENCE: 18

Phe Glu Val Ile Glu Glu Gly Leu Ser Ala Arg Thr Thr Asn Ile
1               5                   10                  15

<210> SEQ ID NO 19
<211> LENGTH: 15
<212> TYPE: PRT
<213> ORGANISM: Mycobacterium smegmatis

<400> SEQUENCE: 19

Ile Glu Glu Gly Leu Ser Ala Arg Thr Thr Asn Ile Asp Asp Pro
1               5                   10                  15

<210> SEQ ID NO 20
<211> LENGTH: 15
<212> TYPE: PRT
<213> ORGANISM: Mycobacterium smegmatis

<400> SEQUENCE: 20

Gly Leu Ser Ala Arg Thr Thr Asn Ile Asp Asp Pro Thr Asp Pro
1               5                   10                  15

<210> SEQ ID NO 21
<211> LENGTH: 15
<212> TYPE: PRT
<213> ORGANISM: Mycobacterium smegmatis

<400> SEQUENCE: 21

Ala Arg Thr Thr Asn Ile Asp Asp Pro Thr Asp Pro Arg Leu Asn
1               5                   10                  15

<210> SEQ ID NO 22
<211> LENGTH: 15
<212> TYPE: PRT
<213> ORGANISM: Mycobacterium smegmatis

<400> SEQUENCE: 22

Thr Asn Ile Asp Asp Pro Thr Asp Pro Arg Leu Asn Gly Ala Ser
1               5                   10                  15

<210> SEQ ID NO 23
<211> LENGTH: 15
```

```
<212> TYPE: PRT
<213> ORGANISM: Mycobacterium smegmatis

<400> SEQUENCE: 23

Asp Asp Pro Thr Asp Pro Arg Leu Asn Gly Ala Ser Tyr Leu Pro
1               5                   10                  15

<210> SEQ ID NO 24
<211> LENGTH: 15
<212> TYPE: PRT
<213> ORGANISM: Mycobacterium smegmatis

<400> SEQUENCE: 24

Thr Asp Pro Arg Leu Asn Gly Ala Ser Tyr Leu Pro Ser Cys Leu
1               5                   10                  15

<210> SEQ ID NO 25
<211> LENGTH: 15
<212> TYPE: PRT
<213> ORGANISM: Mycobacterium smegmatis

<400> SEQUENCE: 25

Arg Leu Asn Gly Ala Ser Tyr Leu Pro Ser Cys Leu Ala Thr His
1               5                   10                  15

<210> SEQ ID NO 26
<211> LENGTH: 15
<212> TYPE: PRT
<213> ORGANISM: Mycobacterium smegmatis

<400> SEQUENCE: 26

Gly Ala Ser Tyr Leu Pro Ser Cys Leu Ala Thr His Leu Pro Leu
1               5                   10                  15

<210> SEQ ID NO 27
<211> LENGTH: 15
<212> TYPE: PRT
<213> ORGANISM: Mycobacterium smegmatis

<400> SEQUENCE: 27

Tyr Leu Pro Ser Cys Leu Ala Thr His Leu Pro Leu Asp Leu Val
1               5                   10                  15

<210> SEQ ID NO 28
<211> LENGTH: 15
<212> TYPE: PRT
<213> ORGANISM: Mycobacterium smegmatis

<400> SEQUENCE: 28

Ser Cys Leu Ala Thr His Leu Pro Leu Asp Leu Val Ile Ile Met
1               5                   10                  15

<210> SEQ ID NO 29
<211> LENGTH: 15
<212> TYPE: PRT
<213> ORGANISM: Mycobacterium smegmatis

<400> SEQUENCE: 29

Ala Thr His Leu Pro Leu Asp Leu Val Ile Ile Met Leu Gly Thr
1               5                   10                  15

<210> SEQ ID NO 30
<211> LENGTH: 15
<212> TYPE: PRT
<213> ORGANISM: Mycobacterium smegmatis
```

<400> SEQUENCE: 30

Leu Pro Leu Asp Leu Val Ile Ile Met Leu Gly Thr Asn Asp Thr
1               5                   10                  15

<210> SEQ ID NO 31
<211> LENGTH: 15
<212> TYPE: PRT
<213> ORGANISM: Mycobacterium smegmatis

<400> SEQUENCE: 31

Asp Leu Val Ile Ile Met Leu Gly Thr Asn Asp Thr Lys Ala Tyr
1               5                   10                  15

<210> SEQ ID NO 32
<211> LENGTH: 15
<212> TYPE: PRT
<213> ORGANISM: Mycobacterium smegmatis

<400> SEQUENCE: 32

Ile Ile Met Leu Gly Thr Asn Asp Thr Lys Ala Tyr Phe Arg Arg
1               5                   10                  15

<210> SEQ ID NO 33
<211> LENGTH: 15
<212> TYPE: PRT
<213> ORGANISM: Mycobacterium smegmatis

<400> SEQUENCE: 33

Leu Gly Thr Asn Asp Thr Lys Ala Tyr Phe Arg Arg Thr Pro Leu
1               5                   10                  15

<210> SEQ ID NO 34
<211> LENGTH: 15
<212> TYPE: PRT
<213> ORGANISM: Mycobacterium smegmatis

<400> SEQUENCE: 34

Asn Asp Thr Lys Ala Tyr Phe Arg Arg Thr Pro Leu Asp Ile Ala
1               5                   10                  15

<210> SEQ ID NO 35
<211> LENGTH: 15
<212> TYPE: PRT
<213> ORGANISM: Mycobacterium smegmatis

<400> SEQUENCE: 35

Lys Ala Tyr Phe Arg Arg Thr Pro Leu Asp Ile Ala Leu Gly Met
1               5                   10                  15

<210> SEQ ID NO 36
<211> LENGTH: 15
<212> TYPE: PRT
<213> ORGANISM: Mycobacterium smegmatis

<400> SEQUENCE: 36

Phe Arg Arg Thr Pro Leu Asp Ile Ala Leu Gly Met Ser Val Leu
1               5                   10                  15

<210> SEQ ID NO 37
<211> LENGTH: 15
<212> TYPE: PRT
<213> ORGANISM: Mycobacterium smegmatis

<400> SEQUENCE: 37

```
Thr Pro Leu Asp Ile Ala Leu Gly Met Ser Val Leu Val Thr Gln
1               5                   10                  15
```

<210> SEQ ID NO 38
<211> LENGTH: 15
<212> TYPE: PRT
<213> ORGANISM: Mycobacterium smegmatis

<400> SEQUENCE: 38

```
Asp Ile Ala Leu Gly Met Ser Val Leu Val Thr Gln Val Leu Thr
1               5                   10                  15
```

<210> SEQ ID NO 39
<211> LENGTH: 15
<212> TYPE: PRT
<213> ORGANISM: Mycobacterium smegmatis

<400> SEQUENCE: 39

```
Leu Gly Met Ser Val Leu Val Thr Gln Val Leu Thr Ser Ala Gly
1               5                   10                  15
```

<210> SEQ ID NO 40
<211> LENGTH: 15
<212> TYPE: PRT
<213> ORGANISM: Mycobacterium smegmatis

<400> SEQUENCE: 40

```
Ser Val Leu Val Thr Gln Val Leu Thr Ser Ala Gly Gly Val Gly
1               5                   10                  15
```

<210> SEQ ID NO 41
<211> LENGTH: 15
<212> TYPE: PRT
<213> ORGANISM: Mycobacterium smegmatis

<400> SEQUENCE: 41

```
Val Thr Gln Val Leu Thr Ser Ala Gly Gly Val Gly Thr Thr Tyr
1               5                   10                  15
```

<210> SEQ ID NO 42
<211> LENGTH: 15
<212> TYPE: PRT
<213> ORGANISM: Mycobacterium smegmatis

<400> SEQUENCE: 42

```
Val Leu Thr Ser Ala Gly Gly Val Gly Thr Thr Tyr Pro Ala Pro
1               5                   10                  15
```

<210> SEQ ID NO 43
<211> LENGTH: 15
<212> TYPE: PRT
<213> ORGANISM: Mycobacterium smegmatis

<400> SEQUENCE: 43

```
Ser Ala Gly Gly Val Gly Thr Thr Tyr Pro Ala Pro Lys Val Leu
1               5                   10                  15
```

<210> SEQ ID NO 44
<211> LENGTH: 15
<212> TYPE: PRT
<213> ORGANISM: Mycobacterium smegmatis

<400> SEQUENCE: 44

```
Gly Val Gly Thr Thr Tyr Pro Ala Pro Lys Val Leu Val Val Ser
```

<210> SEQ ID NO 45
<211> LENGTH: 15
<212> TYPE: PRT
<213> ORGANISM: Mycobacterium smegmatis

<400> SEQUENCE: 45

Thr Thr Tyr Pro Ala Pro Lys Val Leu Val Val Ser Pro Pro Pro
1               5                   10                  15

<210> SEQ ID NO 46
<211> LENGTH: 15
<212> TYPE: PRT
<213> ORGANISM: Mycobacterium smegmatis

<400> SEQUENCE: 46

Pro Ala Pro Lys Val Leu Val Val Ser Pro Pro Pro Leu Ala Pro
1               5                   10                  15

<210> SEQ ID NO 47
<211> LENGTH: 15
<212> TYPE: PRT
<213> ORGANISM: Mycobacterium smegmatis

<400> SEQUENCE: 47

Lys Val Leu Val Val Ser Pro Pro Pro Leu Ala Pro Met Pro His
1               5                   10                  15

<210> SEQ ID NO 48
<211> LENGTH: 15
<212> TYPE: PRT
<213> ORGANISM: Mycobacterium smegmatis

<400> SEQUENCE: 48

Val Val Ser Pro Pro Pro Leu Ala Pro Met Pro His Pro Trp Phe
1               5                   10                  15

<210> SEQ ID NO 49
<211> LENGTH: 15
<212> TYPE: PRT
<213> ORGANISM: Mycobacterium smegmatis

<400> SEQUENCE: 49

Pro Pro Pro Leu Ala Pro Met Pro His Pro Trp Phe Gln Leu Ile
1               5                   10                  15

<210> SEQ ID NO 50
<211> LENGTH: 15
<212> TYPE: PRT
<213> ORGANISM: Mycobacterium smegmatis

<400> SEQUENCE: 50

Leu Ala Pro Met Pro His Pro Trp Phe Gln Leu Ile Phe Glu Gly
1               5                   10                  15

<210> SEQ ID NO 51
<211> LENGTH: 15
<212> TYPE: PRT
<213> ORGANISM: Mycobacterium smegmatis

<400> SEQUENCE: 51

Met Pro His Pro Trp Phe Gln Leu Ile Phe Glu Gly Gly Glu Gln
1               5                   10                  15

```
<210> SEQ ID NO 52
<211> LENGTH: 15
<212> TYPE: PRT
<213> ORGANISM: Mycobacterium smegmatis

<400> SEQUENCE: 52

Pro Trp Phe Gln Leu Ile Phe Glu Gly Gly Glu Gln Lys Thr Thr
1               5                   10                  15

<210> SEQ ID NO 53
<211> LENGTH: 15
<212> TYPE: PRT
<213> ORGANISM: Mycobacterium smegmatis

<400> SEQUENCE: 53

Gln Leu Ile Phe Glu Gly Gly Glu Gln Lys Thr Thr Glu Leu Ala
1               5                   10                  15

<210> SEQ ID NO 54
<211> LENGTH: 15
<212> TYPE: PRT
<213> ORGANISM: Mycobacterium smegmatis

<400> SEQUENCE: 54

Phe Glu Gly Gly Glu Gln Lys Thr Thr Glu Leu Ala Arg Val Tyr
1               5                   10                  15

<210> SEQ ID NO 55
<211> LENGTH: 15
<212> TYPE: PRT
<213> ORGANISM: Mycobacterium smegmatis

<400> SEQUENCE: 55

Gly Glu Gln Lys Thr Thr Glu Leu Ala Arg Val Tyr Ser Ala Leu
1               5                   10                  15

<210> SEQ ID NO 56
<211> LENGTH: 15
<212> TYPE: PRT
<213> ORGANISM: Mycobacterium smegmatis

<400> SEQUENCE: 56

Lys Thr Thr Glu Leu Ala Arg Val Tyr Ser Ala Leu Ala Ser Phe
1               5                   10                  15

<210> SEQ ID NO 57
<211> LENGTH: 15
<212> TYPE: PRT
<213> ORGANISM: Mycobacterium smegmatis

<400> SEQUENCE: 57

Glu Leu Ala Arg Val Tyr Ser Ala Leu Ala Ser Phe Met Lys Val
1               5                   10                  15

<210> SEQ ID NO 58
<211> LENGTH: 15
<212> TYPE: PRT
<213> ORGANISM: Mycobacterium smegmatis

<400> SEQUENCE: 58

Arg Val Tyr Ser Ala Leu Ala Ser Phe Met Lys Val Pro Phe Phe
1               5                   10                  15

<210> SEQ ID NO 59
```

-continued

<211> LENGTH: 15
<212> TYPE: PRT
<213> ORGANISM: Mycobacterium smegmatis

<400> SEQUENCE: 59

Ser Ala Leu Ala Ser Phe Met Lys Val Pro Phe Phe Asp Ala Gly
1               5                   10                  15

<210> SEQ ID NO 60
<211> LENGTH: 15
<212> TYPE: PRT
<213> ORGANISM: Mycobacterium smegmatis

<400> SEQUENCE: 60

Ala Ser Phe Met Lys Val Pro Phe Phe Asp Ala Gly Ser Val Ile
1               5                   10                  15

<210> SEQ ID NO 61
<211> LENGTH: 15
<212> TYPE: PRT
<213> ORGANISM: Mycobacterium smegmatis

<400> SEQUENCE: 61

Met Lys Val Pro Phe Phe Asp Ala Gly Ser Val Ile Ser Thr Asp
1               5                   10                  15

<210> SEQ ID NO 62
<211> LENGTH: 15
<212> TYPE: PRT
<213> ORGANISM: Mycobacterium smegmatis

<400> SEQUENCE: 62

Pro Phe Phe Asp Ala Gly Ser Val Ile Ser Thr Asp Gly Val Asp
1               5                   10                  15

<210> SEQ ID NO 63
<211> LENGTH: 15
<212> TYPE: PRT
<213> ORGANISM: Mycobacterium smegmatis

<400> SEQUENCE: 63

Asp Ala Gly Ser Val Ile Ser Thr Asp Gly Val Asp Gly Ile His
1               5                   10                  15

<210> SEQ ID NO 64
<211> LENGTH: 15
<212> TYPE: PRT
<213> ORGANISM: Mycobacterium smegmatis

<400> SEQUENCE: 64

Ser Val Ile Ser Thr Asp Gly Val Asp Gly Ile His Phe Thr Glu
1               5                   10                  15

<210> SEQ ID NO 65
<211> LENGTH: 15
<212> TYPE: PRT
<213> ORGANISM: Mycobacterium smegmatis

<400> SEQUENCE: 65

Ser Thr Asp Gly Val Asp Gly Ile His Phe Thr Glu Ala Asn Asn
1               5                   10                  15

<210> SEQ ID NO 66
<211> LENGTH: 15
<212> TYPE: PRT

```
<213> ORGANISM: Mycobacterium smegmatis

<400> SEQUENCE: 66

Gly Val Asp Gly Ile His Phe Thr Glu Ala Asn Asn Arg Asp Leu
1               5                   10                  15

<210> SEQ ID NO 67
<211> LENGTH: 15
<212> TYPE: PRT
<213> ORGANISM: Mycobacterium smegmatis

<400> SEQUENCE: 67

Gly Ile His Phe Thr Glu Ala Asn Asn Arg Asp Leu Gly Val Ala
1               5                   10                  15

<210> SEQ ID NO 68
<211> LENGTH: 15
<212> TYPE: PRT
<213> ORGANISM: Mycobacterium smegmatis

<400> SEQUENCE: 68

Phe Thr Glu Ala Asn Asn Arg Asp Leu Gly Val Ala Leu Ala Glu
1               5                   10                  15

<210> SEQ ID NO 69
<211> LENGTH: 15
<212> TYPE: PRT
<213> ORGANISM: Mycobacterium smegmatis

<400> SEQUENCE: 69

Ala Asn Asn Arg Asp Leu Gly Val Ala Leu Ala Glu Gln Val Arg
1               5                   10                  15

<210> SEQ ID NO 70
<211> LENGTH: 15
<212> TYPE: PRT
<213> ORGANISM: Mycobacterium smegmatis

<400> SEQUENCE: 70

Arg Asp Leu Gly Val Ala Leu Ala Glu Gln Val Arg Ser Leu Leu
1               5                   10                  15

<210> SEQ ID NO 71
<211> LENGTH: 45
<212> TYPE: PRT
<213> ORGANISM: Artificial Sequence
<220> FEATURE:
<223> OTHER INFORMATION: synthetic perhydrolase epitope

<400> SEQUENCE: 71

Met Pro His Pro Trp Phe Gln Leu Ile Phe Glu Gly Gly Glu Gln Pro
1               5                   10                  15

Trp Phe Gln Leu Ile Phe Glu Gly Gly Glu Gln Lys Thr Thr Gln Leu
            20                  25                  30

Ile Phe Glu Gly Gly Glu Gln Lys Thr Thr Glu Leu Ala
            35                  40                  45
```

PERHYDROLASE EPITOPES

CROSS-REFERENCE TO RELATED APPLICATIONS

This application is a 371 National Stage entry of International Application No. PCT/US2006/046203, filed Dec. 4, 2006, which claims priority to U.S. Provisional Application No. 60/742,840, filed Dec. 6, 2005, which are incorporated herein by reference in their entireties.

SEQUENCE LISTING

The sequence listing submitted via EFS, in compliance with 37 C.F.R. §1.52(e), is incorporated herein by reference. The sequence listing text file submitted via EFS contains the file "GC895-US-seqlist.txt" created on Oct. 14, 2011, which is 17,482 bytes in size.

FIELD OF THE INVENTION

The present invention provides perhydrolase enzyme CD4+ T-cell epitopes, as well as novel variants that exhibit reduced immunogenic responses, as compared to the parental perhydrolase. The present invention further provides DNA molecules that encode novel perhydrolase variants, and host cells comprising DNA encoding novel perhydrolase variants, as well as methods for making perhydrolase enzymes less immunogenic. In addition, the present invention provides various compositions that comprise perhydrolase variants that are less immunogenic than the wild-type perhydrolase. In some specific embodiments, the present invention provides perhydrolase variants with reduced immunogenicity identified and/or characterized using the methods of the present invention. These enzymes find use in cleaning and other applications. In some preferred embodiments, the present invention finds particular use in applications involving cleaning, bleaching and disinfecting.

BACKGROUND OF THE INVENTION

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes.

Thus, given the wide variety of combinations of components present in cleaning compositions, proteins used in industrial and commercial applications are of increasing prevalence. As a result, the increased exposure due to this prevalence has been responsible for some safety hazards caused by the sensitization of certain persons to those proteins, whereupon subsequent exposure causes extreme allergic reactions which can be injurious and even fatal. For example, proteases are known to cause dangerous hypersensitivity in some individuals. As a result, despite the usefulness of proteases in industry (e.g., in laundry detergents, cosmetics, textile treatment etc.), and the extensive research performed in the field to provide improved proteases which have improved performance (e.g., more effective stain removal under desired detergency conditions), the use of proteases in industry has been problematic due to their ability to produce a hypersensitive immune response in some humans.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of proteases, per se, have been relatively unsuccessful. Alternatively, efforts have been made to mask epitopes in protease which are recognized by immunoglobulin E (IgE) in hypersensitive individuals (See e.g., WO 92/10755) or to enlarge or change the nature of the antigenic determinants by attaching polymers or peptides/proteins to the problematic protease.

However, strategies that involve modifying IgE sites have generally not been successful in preventing the cause of the initial sensitization reaction. Accordingly, such strategies, while perhaps neutralizing or reducing the severity of the subsequent hypersensitivity reaction, do not reduce the number or persons actually sensitized. For example, when a person is known to be hypersensitive to a certain antigen, the general, and only safe, manner of dealing with such a situation is to isolate the hypersensitive person from the antigen as completely as possible. Indeed, any other course of action would be dangerous to the health of the hypersensitive individual. Thus, while reducing the danger of a specific protein for a hypersensitive individual is important, for industrial purposes it would be far more valuable to render a protein incapable of initiating the hypersensitivity reaction in the first place.

The prior art has provided methods of reducing the allergenicity of certain proteins and identification of epitopes which cause allergic reactions in some individuals, the assays used to identify these epitopes generally involving measurement of IgE and IgG antibody in blood sera previously exposed to the antigen. However, once an Ig reaction has been initiated, sensitization has already occurred. Accordingly, there is a need for a method of determining epitopes which cause sensitization in the first place, as neutralization of these epitopes will result in significantly less possibility for sensitization to occur, thus reducing the possibility of initial sensitization.

In addition, despite improvements in the capabilities of cleaning compositions, there remains a need in the art for detergents having enzymes with reduced immunogenicity, but are effective in removing stains, maintaining fabric color and appearance, and preventing dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintenance of the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching, as well as methods and compositions for bleaching in the pulp and paper industry.

Bleaching is also commonly used in the personal care market (e.g., dental whiteners, hair bleachers, etc.). Although personal care bleaching products have improved over the years, there remains a need for mild, easy to use, cost-effective bleaching methods for this setting, particularly those that utilize hypoallergenic constituents.

SUMMARY OF THE INVENTION

The present invention provides perhydrolase enzyme CD4+ T-cell epitopes, as well as novel variants that exhibit reduced immunogenic responses, as compared to the parental perhydrolase. The present invention further provides DNA molecules that encode novel perhydrolase variants, and host cells comprising DNA encoding novel perhydrolase variants, as well as methods for making perhydrolase enzymes less immunogenic. In addition, the present invention provides various compositions that comprise perhydrolase variants that are less immunogenic than the wild-type perhydrolase. In some specific embodiments, the present invention provides perhydrolase variants with reduced immunogenicity identified and/or characterized using the methods of the present invention. These enzymes find use in cleaning and other applications. In some preferred embodiments, the present invention finds particular use in applications involving cleaning, bleaching and disinfecting.

The present invention provides methods for identifying at least one T-cell epitope of perhydrolase, comprising the steps of: (a) obtaining from a from a single human blood source, a solution of dendritic cells and a solution of naïve CD4+ and/or CD8+ T-cells; (b) differentiating the dendritic cells to produce a solution of differentiated dendritic cells; (c) combining the solution of differentiated dendritic cells and the naïve CD4+ and/or CD8+ T-cells with peptide fragments of the perhydrolase; and (d) measuring proliferation of the T-cells in the step (c). In some embodiments, the perhydrolase is a microbial perhydrolase. In some preferred embodiments, the microbial perhydrolase is obtained from an organism selected from the group consisting of Gram-positive microorganisms and Gram-negative microorganisms. In some particularly preferred embodiments, the perhydrolase is a *M. smegmatis* perhydrolase, while in further embodiments, the perhydrolase is an homologue of *M. smegmatis* perhydrolase.

In some alternative embodiments, the perhydrolase comprises at least a portion of the sequence set forth in SEQ ID NO:2. The present invention further provides epitopes identified using the above-described method.

The present invention also provides methods for reducing the immunogenicity of perhydrolase, comprising the steps of: (a) identifying at least one T-cell epitope in the perhydrolase, by (i) contacting an adherent monocyte-derived dendritic cell that has been differentiated by exposure to at least one cytokine in vitro, with at least one peptide comprising the T-cell epitope; and (ii) contacting the dendritic cell and the peptide with a naïve T-cell, wherein the naïve T-cell has been obtained from the same source as the adherent monocyte-derived dendritic cell, and whereby the T-cell proliferates in response to the peptide; and (b) modifying the perhydrolase to neutralize the T-cell epitope to produce a variant perhydrolase, such that the variant perhydrolase induces less than or substantially equal to the baseline proliferation of the naïve T-cells. In some alternative embodiments, the perhydrolase comprises at least a portion of the sequence set forth in SEQ ID NO:2. In some embodiments, the perhydrolase is a microbial perhydrolase. In some preferred embodiments, the microbial perhydrolase is obtained from an organism selected from the group consisting of Gram-positive microorganisms and Gram-negative microorganisms. In some particularly preferred embodiments, the perhydrolase is a *M. smegmatis* perhydrolase, while in further embodiments, the perhydrolase is an homologue of *M. smegmatis* perhydrolase.

In some embodiments, the present invention provides perhydrolase variants produced using the above-described method for production of perhydrolases having reduced immunogenicity.

In some embodiments, the epitope of the perhydrolase is modified by: (a) substituting the amino acid sequence of the T-cell epitope with an analogous sequence from a homolog of the perhydrolase, wherein the substitution substantially mimics the major tertiary structure attributes of the T-cell epitope. In some preferred embodiments, the perhydrolase is modified by altering at least one epitope. In some alternative preferred embodiments, the perhydrolase is modified by altering a perhydrolase epitope sequence selected from the epitope sequences set forth in SEQ ID NOS:51-53, and 71. In some particularly preferred embodiments, the perhydrolase is modified by altering an epitope comprising the sequence set forth in SEQ ID NO:53. In some embodiments, the epitope is modified by substituting an amino acid sequence for a residue corresponding to at least one of the epitopes, while in other embodiments, the epitope is modified by deleting an amino acid sequence for a residue corresponding to at least one of the epitopes, and in still further embodiments, the epitope is modified by adding an amino acid to at least one of the epitopes. The present invention further provides perhydrolases produced using the above method.

The present invention also provides variant perhydrolases comprising at least one alteration in at least one epitope comprising an amino acid sequence. In some particularly preferred embodiments, the immunogenic response produced by the variant perhydrolase is less than the immunogenic response produced by wild-type perhydrolase. However, in some other embodiments, the immunogenic response produced by the variant is greater than the immunogenic response produced by wild-type perhydrolase. In some preferred embodiments, the present invention provides multiple HLA-restricted epitopes that comprise at least a portion of SEQ ID NOS:51-53 (i.e., MPHPWFQLIFEGGEQ PWFQLIFEGGEQKTTQLIFEGGEQKTTELA; SEQ ID NO:71). Indeed, it is contemplated that at least a portion of any of SEQ ID NOS:51-53 and 71 will find use in various embodiments of the present invention. However, it is not intended that the present invention be limited to these specific sequences.

The present invention further provides compositions comprising nucleic acids sequences encoding variant perhydrolases, as well as expression vectors that comprise the nucleic acid, and host cells transformed with the expression vectors.

The present invention still further provides detergents and consumer-related products, including, but not limited to such compositions as personal care compositions that comprise at least one variant perhydrolase of the present invention. In further embodiments, the present invention finds use in paper and pulp bleaching compositions comprising at least one variant perhydrolase. Indeed, various applications, settings, and compositions.

DESCRIPTION OF THE INVENTION

The present invention provides perhydrolase enzyme CD4+ T-cell epitopes, as well as novel variants that exhibit reduced immunogenic responses, as compared to the parental perhydrolase. The present invention further provides DNA molecules that encode novel perhydrolase variants, and host cells comprising DNA encoding novel perhydrolase variants, as well as methods for making perhydrolase enzymes less immunogenic. In addition, the present invention provides various compositions that comprise perhydrolase variants that are less immunogenic than the wild-type perhydrolase. In some specific embodiments, the present invention provides perhydrolase variants with reduced immunogenicity identified and/or characterized using the methods of the present invention. These enzymes find use in cleaning and other applications. In some preferred embodiments, the present invention finds particular use in applications involving cleaning, bleaching and disinfecting.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., *"Molecular Cloning: A Laboratory Manual,"* Second Edition (Cold Spring Harbor) [1989]); and Ausubel et al., *"Current Protocols in Molecular Biology"* [1987]). All patents, patent applications, articles and publications mentioned herein, both supra and infix, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

DEFINITIONS

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Margham, *The Harper Collins Dictionary of Biology*, Harper Perennial, NY (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "bleaching" refers to the treatment of a material (e.g., fabric, laundry, pulp, etc.) or surface for a sufficient length of time and under appropriate pH and temperature conditions to effect a brightening (i.e., whitening) and/or cleaning of the material. Examples of chemicals suitable for bleaching include but are not limited to $ClO_2$, $H_2O_2$, peracids, $NO_2$, etc.

As used herein, the term "disinfecting" refers to the removal of contaminants from the surfaces, as well as the inhibition or killing of microbes on the surfaces of items. It is not intended that the present invention be limited to any particular surface, item, or contaminant(s) or microbes to be removed.

As used herein, the term "perhydrolase" refers to an enzyme that is capable of catalyzing a reaction that results in the formation of sufficiently high amounts of peracid suitable for applications such as cleaning, bleaching, and disinfecting. In particularly preferred embodiments, the perhydrolase enzymes of the present invention produce very high perhydrolysis to hydrolysis ratios. The high perhydrolysis to hydrolysis ratios of these distinct enzymes makes these enzymes suitable for use in a very wide variety of applications. In additional preferred embodiments, the perhydrolases of the present invention are characterized by having distinct tertiary structure and primary sequence. In particularly preferred embodiments, the perhydrolases of the present invention comprises distinct primary and tertiary structures. In some particularly preferred embodiments, the perhydrolases of the present invention comprise distinct quaternary structure. In some preferred embodiments, the perhydrolase of the present invention is the *M. smegmatis* perhydrolase, while in alternative embodiments, the perhydrolase is a variant of this perhydrolase, while in still further embodiments, the perhydrolase is a homolog of this perhydrolase. In further preferred embodiments, a monomeric hydrolase is engineered to produce a multimeric enzyme that has better perhydrolase activity than the monomer. However, it is not intended that the present invention be limited to this specific *M. smegmatis* perhydrolase, specific variants of this perhydrolase, nor specific homologs of this perhydrolase. In some particularly preferred embodiments, the perhydrolase is the *M. smegmatis* perhydrolase described in US04/40438, incorporated herein by reference in its entirety. However, it is not intended that the present invention be limited to this specific *M. smegmatis* perhydrolase, specific variants of this perhydrolase, nor specific homologs of the perhydrolase provided in US04/40438.

As used herein, the term "multimer" refers to two or more proteins or peptides that are covalently or non-covalently associated and exist as a complex in solution. A "dimer" is a multimer that contains two proteins or peptides; a "trimer" contains three proteins or peptides, etc. As used herein, "octamer" refers to a multimer of eight proteins or peptides.

As used herein, "personal care products" means products used in the cleaning, bleaching, and/or disinfecting of hair, skin, scalp, and teeth, including, but not limited to shampoos, body lotions, shower gels, topical moisturizers, toothpaste, and/or other topical cleansers. In some particularly preferred embodiments, these products are utilized on humans, while in other embodiments, these products find use with non-human animals (e.g., in veterinary applications).

As used herein, "pharmaceutically-acceptable" means that drugs, medicaments and/or inert ingredients which the term describes are suitable for use in contact with the tissues of humans and other animals without undue toxicity, incompatibility, instability, irritation, allergic response, and the like, commensurate with a reasonable benefit/risk ratio.

As used herein, "cleaning compositions" and "cleaning formulations" refer to compositions that find use in the removal of undesired compounds from items to be cleaned, such as fabric, dishes, contact lenses, other solid substrates, hair (shampoos), skin (soaps and creams), teeth (mouthwashes, toothpastes) etc. The term encompasses any materials/compounds selected for the particular type of cleaning composition desired and the form of the product (e.g., liquid, gel, granule, or spray composition), as long as the composition is compatible with the perhydrolase and other enzyme(s) used in the composition. The specific selection of cleaning composition materials are readily made by considering the surface, item or fabric to be cleaned, and the desired form of the composition for the cleaning conditions during use.

The terms further refer to any composition that is suited for cleaning, bleaching, disinfecting, and/or sterilizing any object and/or surface. It is intended that the terms include, but are not limited to detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

Indeed, the term "cleaning composition" as used herein, includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

As used herein, the terms "detergent composition" and "detergent formulation" are used in reference to mixtures which are intended for use in a wash medium for the cleaning of soiled objects. In some preferred embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. Indeed, it is intended that in addition to perhydrolase, the term encompasses detergents that contain surfactants, transferase(s), hydrolytic enzymes, oxido reductases, builders, bleaching agents, bleach activators, bluing agents and fluorescent dyes, caking inhibitors, masking agents, enzyme activators, antioxidants, and solubilizers.

As used herein, "enhanced performance" in a detergent is defined as increasing cleaning of bleach-sensitive stains (e.g., grass, tea, wine, blood, dingy, etc.), as determined by usual evaluation after a standard wash cycle. In particular embodiments, the perhydrolase of the present invention provides enhanced performance in the oxidation and removal of colored stains and soils. In further embodiments, the perhydrolase of the present invention provides enhanced performance in the removal and/or decolorization of stains. In yet additional embodiments, the perhydrolase of the present invention provides enhanced performance in the removal of lipid-based stains and soils. In still further embodiments, the perhydrolase of the present invention provides enhanced performance in removing soils and stains from dishes and other items.

As used herein the term "hard surface cleaning composition," refers to detergent compositions for cleaning hard surfaces such as floors, walls, tile, bath and kitchen fixtures, and the like. Such compositions are provided in any form, including but not limited to solids, liquids, emulsions, etc.

As used herein, "dishwashing composition" refers to all forms for compositions for cleaning dishes, including but not limited to granular, liquid and bar forms.

As used herein, "fabric cleaning composition" refers to all forms of detergent compositions for cleaning fabrics, including but not limited to, granular, liquid and bar forms.

As used herein, "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers.

As used herein, "textile materials" is a general term for fibers, yarn intermediates, yarn, fabrics, and products made from fabrics (e.g., garments and other articles).

As used herein, "fabric" encompasses any textile material. Thus, it is intended that the term encompass garments, as well as fabrics, yarns, fibers, non-woven materials, natural materials, synthetic materials, and any other textile material.

As used herein, the term "compatible," means that the cleaning composition materials do not reduce the enzymatic activity of the perhydrolase to such an extent that the perhydrolase is not effective as desired during normal use situations. Specific cleaning composition materials are exemplified in detail hereinafter.

As used herein, "effective amount of perhydrolase enzyme" refers to the quantity of perhydrolase enzyme necessary to achieve the enzymatic activity required in the specific application (e.g., personal care product, cleaning composition, etc.). Such effective amounts are readily ascertained by one of ordinary skill in the art and are based on many factors, such as the particular enzyme variant used, the cleaning application, the specific composition of the cleaning composition, and whether a liquid or dry (e.g., granular, bar) composition is required, and the like. In particularly preferred embodiments, the perhydrolase enzyme has reduced immunogenicity, as compared to other perhydrolase enzymes (e.g., a parent perhydrolase enzyme which has been modified to produce a variant perhydrolase with reduced immunogenicity).

As used herein, "non-fabric cleaning compositions" encompass hard surface cleaning compositions, dishwashing compositions, personal care cleaning compositions (e.g., oral cleaning compositions, denture cleaning compositions, personal cleansing compositions, etc.), and compositions suitable for use in the pulp and paper industry.

As used herein, "oral cleaning compositions" refers to dentifrices, toothpastes, toothgels, toothpowders, mouth-washes, mouth sprays, mouth gels, chewing gums, lozenges, sachets, tablets, biogels, prophylaxis pastes, dental treatment solutions, and the like. Oral care compositions that find use in conjunction with the perhydrolases of the present invention are well known in the art (See e.g., U.S. Pat. Nos. 5,601,750, 6,379,653, and 5,989,526, all of which are incorporated herein by reference).

As used herein, "pulp treatment compositions" refers to the use of the present perhydrolase enzymes in compositions suitable for use in papermaking. It is intended that the term encompass compositions suitable for the treatment of any pulp material, including wood, as well as non-wood materials, such as "agricultural residues" and "fiber crops," including but not limited to wheat straw, rice straw, corn stalks, bagasse (sugar cane), rye grass straw, seed flax straw, flax straw, kenaf, industrial hemp, sisal, textile flat straw, hesperaloe, etc. Thus, the present invention also encompasses the use of the perhydrolases of the present invention in pulp treatment methods.

As used herein, "oxidizing chemical" refers to a chemical that has the capability of bleaching pulp or any other material. The oxidizing chemical is present at an amount, pH and temperature suitable for bleaching. The term includes, but is not limited to hydrogen peroxide and peracids.

As used herein, "acyl" is the general name for organic acid groups, which are the residues of carboxylic acids after removal of the —OH group (e.g., ethanoyl chloride, $CH_3CO$—Cl, is the acyl chloride formed from ethanoic acid, $CH_3COO$—H). The names of the individual acyl groups are formed by replacing the "-ic" of the acid by "-yl."

As used herein, the term "acylation" refers to the chemical transformation which substitutes the acyl (RCO—) group into a molecule, generally for an active hydrogen of an —OH group.

As used herein, the term "transferase" refers to an enzyme that catalyzes the transfer of functional compounds to a range of substrates.

As used herein, "leaving group" refers to the nucleophile which is cleaved from the acyl donor upon substitution by another nucleophile.

As used herein, the term "enzymatic conversion" refers to the modification of a substrate to an intermediate or the modification of an intermediate to an end-product by contacting the substrate or intermediate with an enzyme. In some embodiments, contact is made by directly exposing the substrate or intermediate to the appropriate enzyme. In other embodiments, contacting comprises exposing the substrate or intermediate to an organism that expresses and/or excretes the enzyme, and/or metabolizes the desired substrate and/or intermediate to the desired intermediate and/or end-product, respectively.

As used herein, the phrase "detergent stability" refers to the stability of a detergent composition. In some embodiments, the stability is assessed during the use of the detergent, while in other embodiments, the term refers to the stability of a detergent composition during storage.

As used herein, the phrase, "stability to proteolysis" refers to the ability of a protein (e.g., an enzyme) to withstand proteolysis. It is not intended that the term be limited to the use of any particular protease to assess the stability of a protein.

As used herein, "oxidative stability" refers to the ability of a protein to function under oxidative conditions. In particular, the term refers to the ability of a protein to function in the presence of various concentrations of $H_2O_2$ and/or peracid. Stability under various oxidative conditions can be measured either by standard procedures known to those in the art and/or by the methods described herein. A substantial change in oxidative stability is evidenced by at least about a 5% or greater increase or decrease (in most embodiments, it is preferably an increase) in the half-life of the enzymatic activity, as compared to the enzymatic activity present in the absence of oxidative compounds.

As used herein, "pH stability" refers to the ability of a protein to function at a particular pH. In general, most enzymes have a finite pH range at which they will function. In addition to enzymes that function in mid-range pHs (i.e., around pH 7), there are enzymes that are capable of working under conditions with very high or very low pHs. Stability at various pHs can be measured either by standard procedures known to those in the art and/or by the methods described herein. A substantial change in pH stability is evidenced by at least about 5% or greater increase or decrease (in most embodiments, it is preferably an increase) in the half-life of the enzymatic activity, as compared to the enzymatic activity at the enzyme's optimum pH. However, it is not intended that the present invention be limited to any pH stability level nor pH range.

As used herein, "thermal stability" refers to the ability of a protein to function at a particular temperature. In general, most enzymes have a finite range of temperatures at which they will function. In addition to enzymes that work in mid-range temperatures (e.g., room temperature), there are enzymes that are capable of working in very high or very low temperatures. Thermal stability can be measured either by known procedures or by the methods described herein. A substantial change in thermal stability is evidenced by at least about 5% or greater increase or decrease (in most embodiments, it is preferably an increase) in the half-life of the catalytic activity of a mutant when exposed to a different temperature (i.e., higher or lower) than optimum temperature for enzymatic activity. However, it is not intended that the present invention be limited to any temperature stability level nor temperature range.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability.

As used herein, the phrase "perhydrolase activity improvement" refers to the relative improvement of perhydrolase activity, in comparison with a standard enzyme. In some embodiments; the term refers to an improved rate of perhydrolysis product, while in other embodiments, the term encompasses perhydrolase compositions that produce less hydrolysis product. In additional embodiments, the term refers to perhydrolase compositions with altered substrate specificity.

The term "sample" as used herein is used in its broadest sense. However, in preferred embodiments, the term is used in reference to a sample (e.g., an aliquot) that comprises a peptide (i.e., a peptide within a pepset that comprises a sequence of a protein of interest) that is being analyzed, identified, modified, and/or compared with other peptides. Thus, in most cases, this term is used in reference to material that includes a protein or peptide that is of interest.

As used herein, "Stimulation Index" (SI) refers to a measure of the T-cell proliferative response of a peptide compared to a control. The SI is calculated by dividing the average CPM (counts per minute) obtained in testing the $CD4^+$ T-cell and dendritic cell culture containing a peptide by the average CPM of the control culture containing dendritic cells and $CD4^+$ T-cells but without the peptides. This value is calculated for each donor and for each peptide. While SI values of between about 1.5 to 4.5 may be used to indicate a positive response, the preferred SI value to indicate a positive response is between 2.5 and 3.5, inclusive, preferably between 2.7 and 3.2 inclusive, and more preferably between 2.9 and 3.1 inclusive. The most preferred embodiments described herein use a SI value of 2.95.

As used herein, the term "dataset" as used herein refers to compiled data for a set of peptides and a set of donors for each protein.

As used herein, the term "pepset" refers to the set of peptides obtained from each test protein (i.e., protein of interest). These peptides in the pepset (or "peptide sets") are tested with cells from each donor.

As used herein, "background level" and "background response" refer to the average percent of responders to any given peptide in the dataset for any tested protein. This value is determined by averaging the percent responders for all peptides in the set, as compiled for all the tested donors. As an example, a 3% background response would indicate that on average there would be three positive (SI greater than 2.95) responses for any peptide in a dataset when tested on 100 donors.

As used herein, "antigen presenting cell" ("APC") refers to a cell of the immune system that presents antigen on its surface, such that the antigen is recognizable by receptors on the surface of T-cells. Antigen presenting cells include, but are not limited to dendritic cells, interdigitating cells, activated B-cells and macrophages.

The term "lymphoid" when used in reference to a cell line or a cell, means that the cell line or cell is derived from the lymphoid lineage and includes cells of both the B and the T lymphocyte lineages.

As used herein, the terms "T lymphocyte" and "T-cell," encompass any cell within the T lymphocyte lineage from T-cell precursors (including Thy1 positive cells which have not rearranged the T cell receptor genes) to mature T cells (i.e., single positive for either CD4 or CD8, surface TCR positive cells).

As used herein, the terms "B lymphocyte" and "B-cell" encompasses any cell within the B-cell lineage from B-cell precursors, such as pre-B-cells (B220$^+$ cells which have begun to rearrange Ig heavy chain genes), to mature B-cells and plasma cells.

As used herein, "CD4$^+$ T-cell" and "CD4 T-cell" refer to helper T-cells, while "CD8$^+$ T-cell" and CD8 T-cell" refer to cytotoxic T-cells.

As used herein, "B-cell proliferation," refers to the number of B-cells produced during the incubation of B-cells with the antigen presenting cells, with or without antigen.

As used herein, "baseline B-cell proliferation," as used herein, refers to the degree of B-cell proliferation that is normally seen in an individual in response to exposure to antigen presenting cells in the absence of peptide or protein antigen. For the purposes herein, the baseline B-cell proliferation level is determined on a per sample basis for each individual as the proliferation of B-cells in the absence of antigen.

As used herein, "B-cell epitope," refers to a feature of a peptide or protein that is recognized by a B-cell receptor in the immunogenic response to the peptide comprising that antigen (i.e., the immunogen).

As used herein, "altered B-cell epitope," refers to an epitope amino acid sequence which differs from the precursor peptide or peptide of interest, such that the variant peptide of interest produces different (i.e., altered) immunogenic responses in a human or another animal. It is contemplated that an altered immunogenic response includes altered immunogenicity and/or allergenicity (i.e., an either increased or decreased overall immunogenic response). In some embodiments, the altered B-cell epitope comprises substitution and/or deletion of an amino acid selected from those residues within the identified epitope. In alternative embodiments, the altered B-cell epitope comprises an addition of one or more residues within the epitope.

As used herein "T-cell epitope" means a feature of a peptide or protein that is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II Major Histocompatibility Complex (MHC) molecules expressed on antigen-presenting cells (See e.g., Moeller (ed.), Immunol. Rev., 98:187 [1987]). In some embodiments of the present invention, the epitopes or epitopic fragments identified as described herein find use in the detection of antigen presenting cells having MHC molecules capable of binding and displaying the epitopes or fragments. In some embodiments, the epitopes/epitopic fragments further comprise a detectable label (i.e., a marker) that facilitates the identification of cells that bind and/or display the epitope/epitopic fragment of interest.

As used herein, "T-cell proliferation," refers to the number of T-cells produced during the incubation of T-cells with the antigen presenting cells, with or without antigen.

"Baseline T-cell proliferation," as used herein, refers to the degree of T-cell proliferation that is normally seen in an individual in response to exposure to antigen presenting cells in the absence of peptide or protein antigen. For the purposes herein, the baseline T-cell proliferation level is determined on a per sample basis for each individual as the proliferation of T-cells in response to antigen presenting cells in the absence of antigen.

As used herein "altered immunogenic response," refers to an increased or reduced immunogenic response. Proteins and peptides exhibit an "increased immunogenic response" when the T-cell and/or B-cell response they evoke is greater than that evoked by a parental (e.g., precursor) protein or peptide (e.g., the protein of interest). The net result of this higher response is an increased antibody response directed against the variant protein or peptide. Proteins and peptides exhibit a "reduced immunogenic response" when the T-cell and/or B-cell response they evoke is less than that evoked by a parental (e.g., precursor) protein or peptide. In preferred embodiments, the net result of this lower response is a reduced antibody response directed against the variant protein or peptide. In some preferred embodiments, the parental protein is a wild-type protein or peptide.

As used herein, an "in vivo reduction in immunogenicity" refers to an exhibited decrease in the immunogenic response as determined by an assay that occurs at least in part, within a living organism, (e.g., requires the use of an living animal). Exemplary "in vivo" assays include determination of altered immunogenic responses in mouse models.

As used herein, an "in vitro reduction in immunogenicity" refers an exhibited decrease in the immunogenic response as determined by an assay that occurs in an artificial environment outside of a living organism (i.e., does not require use of a living animal). Exemplary in vitro assays include testing the proliferative responses by human peripheral blood mononuclear cells to a peptide of interest.

As used herein, the term "significant epitope" refers to an epitope (i.e., a T-cell and/or B-cell epitope) wherein the response rate within the tested donor pool is equal to or greater than about three times the background response rate.

As used herein, a "weakly significant epitope" refers to an epitope (i.e., a T-cell and/or B-cell epitope), wherein the response rate within the tested donor pool is greater than the background response rate, but less than about three times the background rate.

As used herein, the phrase "alteration in substrate specificity" refers to changes in the substrate specificity of an enzyme. In some embodiments, a change in substrate specificity is defined as a difference between the $K_{cat}/K_m$ ratio observed with an enzyme compared to enzyme variants or other enzyme compositions. Enzyme substrate specificities vary, depending upon the substrate tested. The substrate specificity of an enzyme is determined by comparing the catalytic efficiencies it exhibits with different substrates. These determinations find particular use in assessing the efficiency of mutant enzymes, as it is generally desired to produce variant enzymes that exhibit greater ratios for particular substrates of interest. For example, the perhydrolase enzymes of the present invention are more efficient in producing peracid from an ester substrate than enzymes currently being used in cleaning, bleaching and disinfecting applications. Another example of the present invention is a perhydrolase with a lower activity on peracid degradation compared to the wild type. Another example of the present invention is a perhydrolase with higher activity on more hydrophobic acyl groups than acetic acid. However, it is not intended that the present invention be limited to any particular substrate composition nor any specific substrate specificity.

As used herein, "surface property" is used in reference to an electrostatic charge, as well as properties such as the hydrophobicity and/or hydrophilicity exhibited by the surface of a protein.

As used herein, the terms "purified" and "isolated" refer to the removal of contaminants from a sample. For example, perhydrolases are purified by removal of contaminating proteins and other compounds within a solution or preparation that are not perhydrolases. In some embodiments, recombinant perhydrolases are expressed in bacterial or fungal host cells and these recombinant perhydrolases are purified by the removal of other host cell constituents; the percent of recombinant perhydrolase polypeptides is thereby increased in the sample.

As used herein, "protein of interest," refers to a protein which is being analyzed, identified and/or modified. Naturally-occurring, as well as recombinant proteins find use in the present invention.

As used herein, "protein" refers to any composition comprised of amino acids and recognized as a protein by those of skill in the art. The terms "protein," "peptide", and polypeptide are used interchangeably herein. Wherein a peptide is a portion of a protein, those skill in the art understand the use of the term in context. The term "protein" encompasses mature forms of proteins, as well as the pro- and prepro-forms of related proteins. Prepro forms of proteins comprise the mature form of the protein having a prosequence operably linked to the amino terminus of the protein, and a "pre-" or "signal" sequence operably linked to the amino terminus of the prosequence. The variants of the present invention include the mature forms of protein variants, as well as the pro- and prepro-forms of such protein variants. The prepro-forms are the preferred construction since this facilitates the expression, secretion and maturation of the protein variants.

As used herein, functionally and/or structurally similar proteins are considered to be "related proteins." In some embodiments, these proteins are derived from a different genus and/or species, including differences between classes of organisms (e.g., a bacterial protein and a fungal protein). In some embodiments, these proteins are derived from a different genus and/or species, including differences between classes of organisms (e.g., a bacterial enzyme and a fungal enzyme). In additional embodiments, related proteins are provided from the same species. Indeed, it is not intended that the present invention be limited to related proteins from any particular source(s). In addition, the term "related proteins" encompasses tertiary structural homologs and primary sequence homologs (e.g., the perhydrolase of the present invention). In further embodiments, the term encompasses proteins that are immunologically cross-reactive. In some most particularly preferred embodiments, the related proteins of the present invention exhibit very high ratios of perhydrolysis to hydrolysis.

As used herein, the term "derivative" refers to a protein which is derived from a protein by addition of one or more amino acids to either or both the C- and N-terminal end(s), substitution of one or more amino acids at one or a number of different sites in the amino acid sequence, and/or deletion of one or more amino acids at either or both ends of the protein or at one or more sites in the amino acid sequence, and/or insertion of one or more amino acids at one or more sites in the amino acid sequence. The preparation of a protein derivative is preferably achieved by modifying a DNA sequence which encodes for the native protein, transformation of that DNA sequence into a suitable host, and expression of the modified DNA sequence to form the derivative protein.

Related (and derivative) proteins comprise "variant proteins." In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between about 1 and about 15. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein, as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

In one embodiment, the prominent corresponding region of a variant produces only a background level of immunogenic response. Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence.

As used herein, the term "analogous sequence" refers to a sequence within a protein that provides similar function, tertiary structure, and/or conserved residues as the protein of interest (i.e., typically the original protein of interest). In particularly preferred embodiments, the analogous sequence involves sequence(s) at or near an epitope. For example, in epitope regions that contain an alpha helix or a beta sheet structure, the replacement amino acids in the analogous sequence preferably maintain the same specific structure. The term also refers to nucleotide sequences, as well as amino acid sequences. In some embodiments, analogous sequences are developed such that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids preferably maintain that specific structure.

As used herein, "homologous protein" refers to a protein (e.g., perhydrolase) that has similar action, structure, antigenic, and/or immunogenic response as a protein of interest (e.g., perhydrolase from another source, such as another strain). It is not intended that homologs be necessarily related evolutionarily. Thus, it is intended that the term encompass the same functional protein obtained from different species. In some preferred embodiments, it is desirable to identify a homolog that has a tertiary and/or primary structure similar to the protein of interest, as replacement for the epitope in the protein of interest with an analogous segment from the homolog will reduce the disruptiveness of the change. Thus, in most cases, closely homologous proteins provide the most desirable sources of epitope substitutions.

Alternatively, it is advantageous to look to human analogs for a given protein. For example, in some embodiments, substituting a specific epitope in one perhydrolase with a sequence from another perhydrolase or other species' perhydrolase results in the production of perhydrolase with reduced immunogenicity. In some preferred embodiments, the perhydrolase homologs of the present invention have tertiary and/or primary structures substantially similar to wild-type perhydrolase. A significant perhydrolase epitope may be replaced with an analogous segment from a homologous enzyme. This type of replacement may reduce the disruptiveness of the change in the parent perhydrolase. In most cases, closely homologous proteins provide the most desirable source of epitope substitutions.

As used herein, "homologous genes" refers to at least a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes). These genes encode "homologous proteins."

As used herein, "ortholog" and "orthologous genes" refer to genes in different species that have evolved from a common ancestral gene (i.e., a homologous gene) by speciation. Typically, orthologs retain the same function in during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

The degree of homology between sequences may be determined using any suitable method known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

For example, PILEUP is a useful program to determine sequence homology levels. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, (Feng and Doolittle, J. Mol. Evol., 35:351-360 [1987]). The method is similar to that described by Higgins and Sharp (Higgins and Sharp, CABIOS 5:151-153 [1989]). Useful PILEUP parameters including a default gap weight of 3.00, a default gap length weight of 0.10, and weighted end gaps. Another example of a useful algorithm is the BLAST algorithm, described by Altschul et al., (Altschul et al., J. Mol. Biol., 215:403-410, [1990]; and Karlin et al., Proc. Natl. Acad. Sci. USA 90:5873-5787 [1993]). One particularly useful BLAST program is the WU-BLAST-2 program (See, Altschul et al., Meth. Enzymol., 266:460-480 [1996]). parameters "W," "T," and "X" determine the sensitivity and speed of the alignment. The BLAST program uses as defaults a wordlength (W) of 11, the BLOSUM62 scoring matrix (See, Henikoff and Henikoff, Proc. Natl. Acad. Sci. USA 89:10915 [1989]) alignments (B) of 50, expectation (E) of 10, M'5, N'-4, and a comparison of both strands.

As used herein, "percent (%) nucleic acid sequence identity" is defined as the percentage of nucleotide residues in a candidate sequence that are identical with the nucleotide residues of the sequence.

The phrases "substantially similar and "substantially identical" in the context of at least two nucleic acids or polypeptides typically means that a polynucleotide or polypeptide comprises a sequence that has at least 60% identity, preferably at least 75% sequence identity, more preferably at least 80%, yet more preferably at least 90%, still more preferably 95%, most preferably 97%, sometimes as much as 98% and 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl. Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "equivalent residues" refers to proteins that share particular amino acid residues. For example, equivalent resides may be identified by determining homology at the level of tertiary structure for a protein (e.g., perhydrolase) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

The present invention encompasses perhydrolases having altered immunogenicity that are equivalent to those that are derived from the particular microbial strain mentioned. Being "equivalent," in this context, means that the perhydrolases are encoded by a polynucleotide capable of hybridizing to a polynucleotide (e.g., SEQ ID NO:1) encoding the amino acid sequence of SEQ ID NO:2 under conditions of medium to high stringency and still retaining the altered immunogenic response to human T-cells. Thus, in some embodiments, equivalent perhydrolases comprise at least 55%, at least 65%, at least 70%, at least 75%, at least 80%, at least 85%, at least 90%, at least 95%, at least 97%, or at least 99% identity to the epitope sequences and the variant perhydrolases having such epitopes.

As used herein, the terms "hybrid perhydrolases" and "fusion perhydrolases" refer to proteins that are engineered from at least two different or "parental" proteins. In preferred embodiments, these parental proteins are homologs of one another. For example, in some embodiments, a preferred hybrid perhydrolase or fusion protein contains the N-terminus of a protein and the C-terminus of a homolog of the protein. In some preferred embodiment, the two terminal ends are combined to correspond to the full-length active protein. In alternative preferred embodiments, the homologs share substantial similarity but do not have identical T-cell epitopes. Therefore, in one embodiment, the present invention provides a perhydrolase of interest having one or more T-cell epitopes in the C-terminus, but in which the C-terminus is replaced with the C-terminus of a homolog having a less potent T-cell epitope, or fewer or no T-cell epitopes in the C-terminus. Thus, the skilled artisan understands that by being able to identify T-cell epitopes among homologs, a variety of variants producing different immunogenic responses can be formed. Moreover, it is understood that internal portions, and more than one homolog can be used to produce the variants of the present invention.

As used herein, "expression vector" refers to a DNA construct containing a DNA sequence that is operably linked to a suitable control sequence capable of effecting the expression of the DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid," "expression plasmid," and "vector" are often used interchangeably as the plasmid is the most commonly used form of vector at present. However, the invention is intended to include such other forms of expression vectors that serve equivalent functions and which are, or become, known in the art.

As used herein, "host cells" are generally prokaryotic or eukaryotic hosts which preferably have been manipulated by the methods known in the art (See e.g., U.S. Pat. No. 4,760,025 (RE 34,606)) to render them incapable of secreting enzymatically active endoprotease. In some preferred embodiments, the host cell used for expressing protein is the *Bacillus* strain BG2036, which is deficient in enzymatically active neutral protein and alkaline protease (subtilisin). The construction of strain BG2036 is described in detail in U.S. Pat. No. 5,264,366, hereby incorporated by reference. Other host cells for expressing protein include *Bacillus subtilis* 1168 (also described in U.S. Pat. No. 4,760,025 (RE 34,606) and U.S. Pat. No. 5,264,366, the disclosures of which are incorporated herein by reference), as well as any suitable *Bacillus* strain, including, but not limited to those within the species of *B. licheniformis, B. lentus*, and other *Bacillus* species, etc. However, it is not intended that the present invention be limited to *Bacillus* species as host cells, as other organisms are known in the art as suitable host cells (e.g., *E. coli*, etc.). In some preferred embodiments, the host cell has been modified such that endogenous perhydrolase produced by the host cell.

Host cells are transformed or transfected with vectors constructed using recombinant DNA techniques known in the art. Transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "introduced" in the context of inserting a nucleic acid sequence into a cell, means transformation, transduction or transfection. Means of transformation include protoplast transformation, calcium chloride precipitation, electroporation, naked DNA and the like as known in the art. (See, Chang and Cohen, Mol. Gen. Genet., 168:111-115 [1979]; Smith et al., Appl. Env. Microbiol., 51:634 [1986]; and the review article by Ferrari et al., in *Bacillus* Harwood (ed.), Plenum Publishing Corporation, pp. 57-52 [1989]).

The term "stable transfection" or "stably transfected" refers to the introduction and integration of foreign DNA into the genome of the transfected cell. The term "stable transfectant" refers to a cell which has stably integrated foreign or exogenous DNA into the genomic DNA of the transfected cell.

The terms "selectable marker" or "selectable gene product" as used herein refer to the use of a gene which encodes an enzymatic activity that confers resistance to an antibiotic or function at high temperature, are found to display high specificity for the sequences bounded and thus defined by the primers; the high temperature results in thermodynamic conditions that favor primer hybridization with the target sequences and not hybridization with non-target sequences.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double-stranded DNA at or near a specific nucleotide sequence.

As indicated above, the perhydrolases of the present invention exhibit modified immunogenic responses (e.g., antigenicity and/or immunogenicity) when compared to the native perhydrolases encoded by their precursor DNAs. In some preferred embodiments, the proteins (e.g., perhydrolases) exhibit reduced allergenicity/immunogenicity. Those of skill in the art readily recognize that the uses of the perhydrolases of this invention will be determined, in large part, on the immunological properties of the proteins.

In another embodiment, the epitopic fragments herein are used in the detection of antigen presenting cells having MHC molecules capable of binding and displaying such fragments. For example, the epitopic fragments can include a detectable label (e.g., radiolabel). The labeled fragments are then incubated with cells of interest, and then cells which bind (or display) the labeled fragments are detected.

In additional embodiments, the related and/or variant perhydrolases with reduced allergenicity/immunogenicity find use in other applications, including pharmaceutical applications, drug delivery applications, cancer treatment regimens, and other health care applications, as well as personal care applications. Indeed, it is contemplated that the perhydrolases of the present invention will find widespread use in numerous compositions and applications.

Several methods are known in the art that are suitable for generating variants of the perhydrolase enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

In some preferred embodiments, the perhydrolase gene is ligated into an appropriate expression plasmid. The cloned perhydrolase gene is then used to transform or transfect a host cell in order to express the perhydrolase gene. This plasmid may replicate in hosts in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the perhydrolase gene. In some embodiments, a selection gene such as an antibiotic resistance gene that enables continuous cultural maintenance of plasmid-infected host cells by growth in antimicrobial-containing media is also included.

The following cassette mutagenesis method may be used to facilitate the construction of the perhydrolase variants of the present invention, although other methods may be used.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

The terms "nucleic acid molecule encoding," "nucleic acid sequence encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, "wild-type" and "native" proteins are those found in nature. The terms "wild-type sequence," and "wild-type gene" are used interchangeably herein, to refer to a sequence that is native or naturally occurring in a host cell. In some embodiments, the wild-type sequence refers to a sequence of interest that is the starting point of a protein engineering project. The genes encoding the naturally-occurring protein may be obtained in accord with the general methods known to those skilled in the art. The methods generally comprise synthesizing labeled probes having putative sequences encoding regions of the protein of interest, preparing genomic libraries from organisms expressing the protein, and screening the libraries for the gene of interest by hybridization to the probes. Positively hybridizing clones are then mapped and sequenced.

The term "recombinant DNA molecule" as used herein refers to a DNA molecule that is comprised of segments of DNA joined together by means of molecular biological techniques.

The term "recombinant oligonucleotide" refers to an oligonucleotide created using molecular biological manipulations, including but not limited to, the ligation of two or more oligonucleotide sequences generated by restriction enzyme digestion of a polynucleotide sequence, the synthesis of oligonucleotides (e.g., the synthesis of primers or oligonucleotides) and the like.

As used herein, the term "hybridization" refers to the process by which a strand of nucleic acid joins with a complementary strand through base pairing, as known in the art.

As used herein, the phrase "hybridization conditions" refers to the conditions under which hybridization reactions are conducted. These conditions are typically classified by degree of "stringency" of the conditions under which hybridization is measured. The degree of stringency can be based, for example, on the melting temperature (Tm) of the nucleic acid binding complex or probe. For example, "maximum stringency" typically occurs at about Tm−5° C. (5° below the Tm of the probe); "high stringency" at about 5-10° below the Tm; "intermediate stringency" at about 10-20° below the Tm of the probe; and "low stringency" at about 20-25° below the Tm. Alternatively, or in addition, hybridization conditions can be based upon the salt or ionic strength conditions of hybridization and/or one or more stringency washes. For example, 6×SSC=very low stringency; 3×SSC=low to medium stringency; 1×SSC=medium stringency; and 0.5× SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe.

For applications requiring high selectivity, it is typically desirable to use relatively stringent conditions to form the hybrids (e.g., relatively low salt and/or high temperature conditions are used).

The Present Invention

The present invention provides perhydrolase enzyme CD4+ T-cell epitopes, as well as novel variants that exhibit reduced immunogenic responses, as compared to the parental perhydrolase. The present invention further provides DNA molecules that encode novel perhydrolase variants, and host cells comprising DNA encoding novel perhydrolase variants, as well as methods for making perhydrolase enzymes less immunogenic. In addition, the present invention provides various compositions that comprise perhydrolase variants that are less immunogenic than the wild-type perhydrolase. In some specific embodiments, the present invention provides perhydrolase variants with reduced immunogenicity that identified and/or characterized using the methods of the present invention. These enzymes find use in cleaning and other applications. In some preferred embodiments, the present invention finds particular use in applications involving cleaning, bleaching and disinfecting.

In some most particularly preferred embodiments, the present invention finds use in the enzymatic generation of peracids from ester substrates and hydrogen peroxide through the use of perhydrolase enzymes with reduced immunogenicity. In some preferred embodiments, the substrates are selected from one or more of the following: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Importantly, the present invention provides means for effective cleaning, bleaching, and disinfecting over broad pH and temperature ranges. In some embodiments, the pH range utilized in this generation is 4-12. In alternative embodiments, the temperature range utilized is between 5° and 90° C. The present invention provides advantages over the presently used systems (See e.g., EP Appln. 87-304933.9) in that bleaching is possible at the optimum pH of peracid oxidation, as well as providing bleaching at neutral pH, acidic pHs, and at low temperatures. While the present invention is described herein most fully in regard to laundry and fabric care, it is not intended that the present invention be limited to these applications. Indeed, the present invention finds use in various settings, particularly those in which bleaching by peracids and/or hydrogen peroxide are desired, including but not limited to laundry, fabric treatment, pulp and paper processing, personal care applications, disinfection and cleaning of hard surfaces. For example, it is contemplated that the compositions of the present invention will find use in bleaching of pulp, including use, in methods such as those set forth in U.S. Pat. Nos. 6,569,286, 5,785,812, 6,165,318, and 4,400,237, all of which are herein incorporated by reference.

Historically, sodium perborate, and more recently sodium percarbonate, have been used as bleaching compounds, particularly in European laundry detergents. This compound decomposes rapidly in aqueous solution to yield hydrogen peroxide ($H_2O_2$), which is the active bleaching species. As sodium perborate is more active at temperatures above 80° C., and less active in the temperature range of 40-60° C. (i.e., wash temperatures that have become most commonly preferred as of the 1950s), bleaching activators have been incorporated into laundry detergents that contain sodium perborate. Indeed, most laundry detergents contain bleaching activators. These activators are compounds with O- or N-bounded acetyl groups that are able to react with the strongly nucleophilic hydroperoxy anion to yield peroxyacetic acid. Since the reacting species is hydroperoxy anion, alkaline pHs are essential for the efficient conversion of these activators to peracids. The peroxyacetic acid is decomposed in weakly basic media to form singlet oxygen (See, Hofmann et al., J. Prakt. Chem., 334:293-297 [1992]).

Hydrogen peroxide is a particularly effective bleach at high temperatures (e.g., >40° C.) and pH (>10), conditions that are typically used in washing fabrics in some settings. However, as indicated above, cold water washing is becoming more commonly used and results in less effective bleaching by $H_2O_2$ than use of hot water. To overcome this low temperature disadvantage, detergent formulations typically include bleach boosters, such as TAED (N,N,N'N'-tetraacetylethylenediamine), NOBS (nonanoyloxybenzene sulfonate), etc. These boosters combine with $H_2O_2$ to form peracetic acid, a peracid species that is more effective than $H_2O_2$ alone. Although it helps the bleaching capability of detergent, the TAED reaction is only approximately 50% efficient, as only two out of the four acetyl groups in TAED are converted to peracids. Additionally, conversion of TAED into peracetic acid by hydrogen peroxide is efficient only at alkaline pHs and high temperatures. Thus, the TAED reaction is not optimized for use in all bleaching applications (e.g., those involving neutral or acidic pHs, and cold water). The present invention provides means to overcome the disadvantages of TAED use, as well as providing the advantage of an enzyme that has reduced immunogenicity. For example, the present invention finds use in cold water applications, as well as those involving neutral or acidic pH levels. Furthermore, the present invention provides means for peracid generation from hydrogen peroxide, with a high perhydrolysis to hydrolysis ratio. The present invention further provides advantages over compositions that contain enzymes such as esterases and lipases) which have very low perhydrolysis to hydrolysis ratios.

In addition to its applications in detergents, the present invention provides methods and compositions for the use of peracids in textile bleaching and in various other applications. In some embodiments, the present invention provides one-step methods for textile processing applications, including but not limited to one-step desizing, scouring and bleaching processes (See e.g., EP WO 03002810, EP 1255888, WO 0164993, and US 20020007516, all of which are hereby incorporated by reference). As described in greater detail herein, in some embodiments, bleaching involves processing textile material before it is dyed and/or after it is incorporated into textile goods. However, it is not intended that the present invention be limited to any particular regimen of use nor any particular textile material.

Furthermore, the peracetic technology of the present invention finds use as an effective bactericide (See, Baldry, J. Appl. Bacteriol., 54:417-423 [1983]). Thus, the present invention provides compositions and methods for the sterilization/disinfection of various objects, including but not limited to medical devices, medical equipment, industrial equipment, and fermenters, as well as any additional object that needs to be sterilized or disinfected. As discussed in greater detail below, during the development of the present invention, the enzyme of the present invention was used in a standard cell kill experiment to demonstrate this suitability. In additional embodiments, the present invention provides compositions and methods suitable for use in biofilm control, such as in cooling towers.

The present invention provides many advantages for cleaning and/or sterilization of a wide range of objects, including but not limited to clothing, fabrics, medical devices, etc. In addition, the present invention provides compositions having perhydrolase enzymes with reduced immunogenicity, but that are effective in cleaning, bleaching, and disinfecting, over a range of wash temperatures and pHs. In additional embodiments, the present invention finds use in degradation of peracids through the perhydrolase peracid degradation activity. In some preferred embodiments, this activity is used in peracid waste clean up applications.

Furthermore, the perhydrolase enzymes of the present invention are active on various acyl donor substrates, as well as being active at low substrate concentrations, and provide means for efficient perhydrolysis due to the high peracid:acid ratio. Indeed, it has been recognized that higher perhydrolysis to hydrolysis ratios are preferred for bleaching applications (See e.g., U.S. Pat. Nos. 5,352,594, 5,108,457, 5,030,240, 3,974,082, and 5,296,616, all of which are herein incorporated by reference). In preferred embodiments, the perhydrolase enzymes of the present invention provide perhydrolysis to hydrolysis ratios that are greater than 1. In particularly preferred embodiments, the perhydrolase enzymes provide a perhydrolysis to hydrolysis ratio greater than 1 and are find use in bleaching.

In addition, it has been shown to be active in commonly used detergent formulations (e.g., Ariel Futur, WOB, etc.). Thus, the present invention provides many advantages in various cleaning settings.

As indicated above, key components to peracid production by enzymatic perhydrolysis are enzyme, ester substrate, and hydrogen peroxide. Hydrogen peroxide can be either added directly in batch, or generated continuously "in situ." Current washing powders use batch additions of $H_2O_2$, in the form of percarbonate or perborate salts that spontaneously decompose to $H_2O_2$. The perhydrolase enzymes of the present invention find use in the same washing powder batch method as the $H_2O_2$ source. However, these enzymes also find use with any other suitable source of $H_2O_2$, including that generated by chemical, electrochemical, and/or enzymatic means. Examples of chemical sources are the percarbonates and perborates mentioned above, while an example of an electrochemical source is a fuel cell fed oxygen and hydrogen gas, and an enzymatic example includes production of $H_2O_2$ from the reaction of glucose with glucose oxidase. The following equation provides an example of a coupled system that finds use with the present invention.

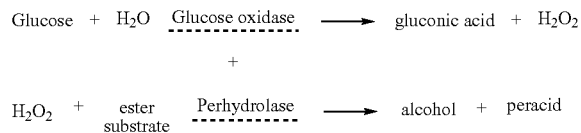

It is not intended that the present invention be limited to any specific enzyme, as any enzyme that generates $H_2O_2$ with a suitable substrate finds use in the methods of the present invention. For example, lactate oxidases from *Lactobacillus* species which are known to create $H_2O_2$ from lactic acid and oxygen find use with the present invention. Indeed, one advantage of the methods of the present invention is that the generation of acid (e.g., gluconic acid in the above example) reduces the pH of a basic solution to the pH range in which the peracid is most effective in bleaching (i.e., at or below the pKa). Other enzymes (e.g., alcohol oxidase, ethylene glycol oxidase, glycerol oxidase, amino acid oxidase, etc.) that can generate hydrogen peroxide also find use with ester substrates in combination with the perhydrolase enzymes of the present invention to generate peracids. In some preferred embodiments, the ester substrates are selected from one or more of the following acids: formic acid, acetic acid, propionic acid, butyric acid, valeric acid, caproic acid, caprylic acid, nonanoic acid, decanoic acid, dodecanoic acid, myristic acid, palmitic acid, stearic acid, and oleic acid. Thus, as described herein, the present invention provides definite advantages over the currently used methods and compositions for detergent formulation and use, as well as various other applications. Importantly, the present invention provides perhydrolase enzymes that have reduced immunogenicity than wild-type perhydrolases. However, it is not intended that the present invention be limited to any particular perhydrolases or any particular epitope modifications. Indeed, it is contemplated that perhydrolases having multiple T-cell epitope modifications, as well as or in addition to at least one B-cell epitope modifications will find use in the present invention. Thus, the approaches for modifying T-cell and/or B-cell epitopes.

EXPERIMENTAL

The following Examples serve to illustrate certain preferred embodiments and aspects of the present invention and are not to be construed as limiting the scope thereof.

In the experimental disclosure which follows, the following abbreviations apply: sd and SD (standard deviation); ° C. (degrees Centigrade); rpm (revolutions per minute); $H_2O$ (water); HCl (hydrochloric acid); aa (amino acid); bp (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris (tris(hydroxymethyl)aminomethane); TAED (N,N,N'N'-tetraacetylethylenediamine); w/v (weight to volume); v/v (volume to volume); Per (perhydrolase); per (perhydrolase gene); Ms (*M. smegmatis*); MS (mass spectroscopy); BRAIN (BRAIN Biotechnology Research and Information Network, AG, Zwingenberg, Germany); TIGR (The Institute for Genomic Research, Rockville, Md.); AATCC (American Association of Textile and Coloring Chemists); WFK (wfk Testgewebe GmbH, Bruggen-Bracht, Germany); Amersham (Amersham Life Science, Inc. Arlington Heights, Ill.); ICN (ICN Pharmaceuticals, Inc., Costa Mesa, Calif.); Pierce (Pierce Biotechnology, Rockford, Ill.); Amicon (Amicon, Inc., Beverly, Mass.); ATCC (American Type Culture Collection, Manassas, Va.); Amersham (Amersham Biosciences, Inc., Piscataway, N.J.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Novagen (Novagen, Inc., Madison, Wis.); Qiagen (Qiagen, Inc., Valencia, Calif.); Invitrogen (Invitrogen, Corp., Carlsbad, Calif.); Genaissance (Genaissance Pharmaceuticals, Inc., New Haven, Conn.); DNA 2.0 (DNA 2.0, Menlo Park, Calif.); MIDI (MIDI Labs, Newark, Del.) InvivoGen (InvivoGen, San Diego, Calif.); Sigma (Sigma Chemical Co., St. Louis, Mo.); Sorvall (Sorvall Instruments, a subsidiary of DuPont Co., Biotechnology Systems, Wilmington, Del.); Stratagene (Stratagene Cloning Systems, La Jolla, Calif.); Roche (Hoffmann La Roche, Inc., Nutley, N.J.); Agilent (Agilent Technologies, Palo Alto, Calif.); Minolta (Konica Minolta, Ramsey, N.J.); and Zeiss (Carl Zeiss, Inc., Thornwood, N.Y.).

All peptides were obtained from a commercial source (Mimotopes, San Diego, Calif.). For the I-MUNE® assay system described herein, 15-mer peptides offset by 3 amino acids that described the entire sequence of the proteins of interest were synthesized in a multipin format (See, Maeji et al., J. Immunol. Meth., 134:23-33 [1990]). Peptides were resuspended in DMSO at approximately 1 to 2 mg/ml, and stored at −70° C. prior to use. Each peptide was tested at least in duplicate. The results for each peptide were averaged. In some cases, the stimulation index (SI) was calculated for each peptide.

Human Donor Blood Samples

Volunteer donor human blood buffy coat samples were obtained from two commercial sources (Stanford Blood Center, Palo Alto, Calif., and the Sacramento Medical Foundation, Sacramento, Calif.). Buffy coat samples were further purified by density separation. Each sample was HLA typed for HLA-DR and HLA-DQ using a commercial PCR-based kit (Bio-Synthesis). The HLA DR and DQ expression in the donor pool was determined to not be significantly different from a North American reference standard (Mori et al., Transplant., 64:1017-1027 [1997]). However, the donor pool did show evidence of slight enrichments for ethnicities common to the San Francisco Bay Area.

Data Analysis

For each individual buffy coat sample, the average CPM values for all of the peptides were analyzed. The average CPM values for each peptide were divided by the average CPM value for the control (DMSO only) wells to determine the "stimulation index" (SI). Donors were tested with each peptide set until an average of at least two responses per peptide were compiled. The data for each protein was graphed showing the percent responders to each peptide within the set. A positive response was collated if the SI value was equal to or greater than 2.95. This value was chosen as it approximates a difference of three standard deviations in a normal population distribution. For each protein assessed, positive responses to individual peptides by individual donors were compiled. To determine the background response for a given protein, the percent responders for each peptide in the set were averaged and a standard deviation was calculated. Statistical significance was calculated using Poisson statistics for the number of responders to each peptide within the dataset. Different statistical methods were used as described herein. The response to a peptide was considered significant if either the number of donors responding to the peptide was different from the Poisson distribution defined by the dataset with a p<0.05 and/or if the percent response was at least 3-fold greater than the background.

Statistical Methods

Statistical significance of peptide responses were calculated based on Poisson statistics. The average frequency of responders was used to calculate a Poisson distribution based on the total number of responses and the number of peptides in the set. A response was considered significant if p<0.05. In addition, two-tailed Student's t-tests with unequal variance, were performed. For epitope determination using data with low background response rates, a conservative Poisson based formula was applied:

$$= 1 - e\left(-n\left(1 - \sum \frac{\lambda^x e^{-\lambda}}{x!}\right)\right)$$

where n=the number of peptides in the set, x=the frequency of responses at the peptide of interest, and λ=the median frequency of responses within the dataset. For epitope determinations based on data with a high background response rate, the less stringent Poisson based determination $$1 - \left(\sum_{i=0}^{x} \frac{\lambda^x e^{-\lambda}}{x!}\right)$$

was used, where λ=the median frequency of responses in the dataset, and x=the frequency of responses at the peptide of interest.

In additional embodiments, the structure determination is calculated based on the following formula:

$$\Sigma \left| f(i) - \frac{1}{p} \right|$$

wherein Σ (upper case sigma) is the sum of the absolute value of the frequency of responses to each peptide minus the frequency of that peptide in the set; f(i) is defined as the frequency of responses for an individual peptide; and p is the number of peptides in the peptide set.

This equation returns a value between 0 and 2, which is equal to the "Structure Value" ("Structure Index"; "Structure Index Value") A value of 0 indicates that the results are completely without structure, and a value of 2.0 indicates all structure is highly structured around a single area. The closer the value is to 2.0, the more immunogenic the protein. Thus, a low value indicates a less immunogenic protein. The relative immunogenicity of perhydrolase, based on its structure index value was not quite 0.5. Thus, its relative immunogenicity was lower than various other enzymes (See e.g., U.S. patent application Ser. No. 10/502,818, filed Feb. 26, 2003, herein incorporated by reference in its entirety).

HLA Types within the Donor Pool

Previously, HLA-DR and DQ types were analyzed for associations with responses to defined epitope peptides. A Chi-squared analysis, with one degree of freedom was used to determine significance. Where an allele was present in both the responder and non-responder pools, a relative risk was calculated.

The HLA-DRB1 allelic expression was determined for approximately 84 random individuals. HLA typing was performed using low-stringency PCR determinations. PCR reactions were performed as directed by the manufacturer (Bio-Synthesis). The data compiled for the Stanford and Sacramento samples were compared the "Caucasian" HLA-DRB1 frequencies as published (See, Marsh et al., *HLA Facts Book, The*. Academic Press, San Diego, Calif. [2000], page 398, FIG. 1). The donor population in these communities is enriched for HLA-DR4 and HLA-DR15. However, the frequencies of these alleles in these populations are well within the reported range for these two alleles (5.2 to 24.8% for HLA-DR4 and 5.7 to 25.6% for HLA-DR15). Similarly, for HLA-DR3, -DR7 and DR11, the frequencies are lower than the average Caucasian frequency, but within the reported ranges for those alleles. Also of note, HLA DR15 is found at a higher frequency in ethnic populations that are heavily represented in the San Francisco Bay Area.

EXAMPLE 1

Preparation of Cells Used in the I-MUNE® Assay System for the Identification of Peptide T-Cell Epitopes in Perhydrolase Using Human T-Cells Fresh human peripheral blood cells were collected from 69 humans of unknown exposure status to perhydrolase. These cells were tested to determine antigenic epitopes in perhydrolase, as described in Example 3.

Peripheral mononuclear blood cells (stored at room temperature, no older than 24 hours) were prepared for use as follows. For each sample, approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature Lymphoprep density separation media (Nycomed; Pharma AS; Density 1.077 g/ml). The tubes were centrifuged for thirty minutes at 600×g. The interface of the two phases was collected, pooled and washed in DPBS. The cell density of the resultant solution was measured by hemocytometer, as known in the art. Viability was measured by trypan blue exclusion, as known in the art.

From the resulting solution, a differentiated dendritic cell culture was prepared from the peripheral blood mononuclear cell sample having a density of $10^8$ cells per 75 ml culture flask in a solution as described below:
 (1) 50 mls of serum free AIM V media (Gibco) was supplemented with a 1:1000 dilution beta-mercaptoethanol (Gibco). The flasks were laid flat for two hours at 37° C. in 5% $CO_2$ to allow adherence of monocytes to the flask wall.
 (2) Differentiation of the monocyte cells to dendritic cells was performed as follows: non-adherent cells were removed and the resultant adherent cells (monocytes) combined with 30 ml of AIM V, 800 units/ml of GM-CSF (Endogen) and 500 units/ml of IL-4 (Endogen); the resulting mixture was cultured for 5 days at 37° C. in 5% $CO_2$. After the five days of incubation, the cytokine TNFα (Endogen) was added to 0.2 units/ml, and the cytokine IL-1α (Endogen) was added to a final concentration of 50 units/ml and the mixture incubated at 37° C. in 5% $CO_2$ for two more days.
 (3) On the seventh day, mitomycin C was added to a concentration of 50 micrograms/ml in 100 mM EDTA-containing PBS to stop growth of the now differentiated dendritic cell culture. The solution was incubated for 60 minutes at 37° C. in 5% $CO_2$. Dendritic cells were dislodged from the plastic surface by gently rapping the flask. Dendritic cells were then centrifuged at 600×g for 5 minutes, washed in DPBS and counted as described above.
 (4) The prepared dendritic cells were placed into a 96 well round bottom plate at a concentration of $2×10^4$ cells/well in 100 microliter total volume of AIM V media, per well.

CD4+ T cells were prepared from frozen aliquots of the peripheral blood cell samples used to prepare the dendritic cells, using reagents provided by the Dynal CD4+ T-cell enrichment kit (Dynal). The resultant CD4+ cell solution was centrifuged, resuspended in AIMV media and the cell density was determined using methods known in the art. The CD4+ T-cell suspension was then resuspended to a count of $2×10^6$/ml in AIM V media to facilitate efficient manipulation of 96-well plates.

EXAMPLE 2

Identification of T-Cell Epitopes in Perhydrolase

Peptides for use in the I-MUNE® assay described in Example 3 were prepared based on the sequence of *M. smegmatis* perhydrolase shown below:

(SEQ ID NO: 2)
MAKRILCFGDSLTWGWVPVEDGAPTERFAPDVRWTGVLAQQLGADFEVIE
EGLSARTTNIDDPTDPRLNGASYLPSCLATHLPLDLVIIMLGTNDTKAYF
RRTPLDIALGMSVLVTQVLTSAGGVGTTYPAPKVLVVSPPPLAPMPHPWF
QLIFEGGEQKTTELARVYSALASFMKVPFFDAGSVISTDGVDGIHFTEAN
NRDLGVALAEQVRSLL

In some embodiments, this sequence is encoded by the following nucleic acid sequence:

(SEQ ID NO: 1)
5'-ATGGCCAAGCGAATTCTGTGTTTCGGTGATTCCCTGACCTGGGGCTG

GGTCCCCGTCGAAGACGGGGCACCCACCGAGCGGTTCGCCCCCGACGTGC

GCTGGACCGGTGTGCTGGCCCAGCAGCTCGGAGCGGACTTCGAGGTGATC

GAGGAGGGACTGAGCGCGCGCACCACCAACATCGACGACCCCACCGATCC

GCGGCTCAACGGCGCGAGCTACCTGCCGTCGTGCCTCGCGACGCACCTGC

CGCTCGACCTGGTGATCATCATGCTGGGCACCAACGACACCAAGGCCTAC

TTCCGGCGCACCCCGCTCGACATCGCGCTGGGCATGTCGGTGCTCGTCAC

GCAGGTGCTCCCAGCGCGGGCGGCGTCGGCACCACGTACCCGGCACCCAA

GGTGCTGGTGGTCTCGCCGCCACCGCTGGCGCCCATGCCGCACCCCTGGT

TCCAGTTGATCTTCGAGGGCGGCGAGCAGAAGACCACTGAGCTCGCCCGC

GTGTACAGCGCGCTCGCGTCGTTCATGAAGGTGCCGTTCTTCGACGCGGG

TTCGGTGATCAGCACCGACGGCGTCGACGGAATCCACTTCACCGAGGCCA

ACAATCGCGATCTCGGGGTGGCCCTCGCGGAACAGGTGCGGAGCCTGCTG

TAA-3'

Based upon the amino acid sequence of the *M. smegmatis* perhydrolase provided above, a set of 15 mers off-set by three amino acids comprising the entire sequence of the perhydrolase were synthetically prepared by Mimotopes. Additional peptides are included in this table. The sequences of these peptides are provided below:

TABLE 1

| Peptides Tested in I-MUNE ® Assay | |
|---|---|
| SEQUENCE | SEQUENCE ID NO. |
| MAKRILCFGDSLTWG | SEQ ID NO: 3 |
| RILCFGDSLTWGWVP | SEQ ID NO: 4 |
| CFGDSLTWGWVPVED | SEQ ID NO: 5 |
| DSLTWGWVPVEDGAP | SEQ ID NO: 6 |
| TWGWVPVEDGAPTER | SEQ ID NO: 7 |
| WVPVEDGAPTERFAP | SEQ ID NO: 8 |
| VEDGAPTERFAPDVR | SEQ ID NO: 9 |
| GAPTERFAPDVRWTG | SEQ ID NO: 10 |
| TERFAPDVRWTGVLA | SEQ ID NO: 11 |
| FAPDVRWTGVLAQQL | SEQ ID NO: 12 |
| DVRWTGVLAQQLGAD | SEQ ID NO: 13 |

TABLE 1-continued

Peptides Tested in I-MUNE® Assay

| SEQUENCE | SEQUENCE ID NO. |
|---|---|
| WTGVLAQQLGADFEV | SEQ ID NO: 14 |
| VLAQQLGADFEVIEE | SEQ ID NO: 15 |
| QQLGADFEVIEEGLS | SEQ ID NO: 16 |
| GADFEVIEEGLSART | SEQ ID NO: 17 |
| FEVIEEGLSARTTNI | SEQ ID NO: 18 |
| IEEGLSARFINIDDP | SEQ ID NO: 19 |
| GLSARTTNIDDPTDP | SEQ ID NO: 20 |
| ARTTNIDDPTDPRLN | SEQ ID NO: 21 |
| TNIDDPTDPRLNGAS | SEQ ID NO: 22 |
| DDPTDPRLNGASYLP | SEQ ID NO: 23 |
| TDPRLNGASYLPSCL | SEQ ID NO: 24 |
| RLNGASYLPSCLATH | SEQ ID NO: 25 |
| GASYLPSCLATHLPL | SEQ ID NO: 26 |
| YLPSCLATHLPLDLV | SEQ ID NO: 27 |
| SCLATHLPLDLVIIM | SEQ ID NO: 28 |
| ATHLPLDLVIIMLGT | SEQ ID NO: 29 |
| LPLDLVIIMLGTNDT | SEQ ID NO: 30 |
| DLVIIMLGTNDTKAY | SEQ ID NO: 31 |
| IIMLGTNDTKAYFRR | SEQ ID NO: 32 |
| LGTNDTKAYFRRTPL | SEQ ID NO: 33 |
| NDTKAYFRRTPLDIA | SEQ ID NO: 34 |
| KAYPRRTPLDIALGM | SEQ ID NO: 35 |
| FRRTPLDLALGMSVL | SEQ ID NO: 36 |
| TPLDIALGMSVLVTQ | SEQ ID NO: 37 |
| DIALGMSVLVTQVLT | SEQ ID NO: 38 |
| LGMSVLVTQVLTSAG | SEQ ID NO: 39 |
| SVLVTQVLTSAGGVG | SEQ ID NO: 40 |
| VTQVLTSAGGVGTTY | SEQ ID NO: 41 |
| VLTSAGGVGTTYPAP | SEQ ID NO: 42 |
| SAGGVGTTYPAPKVL | SEQ ID NO: 43 |
| GVGTTYPAPKVLVVS | SEQ ID NO: 44 |
| TTYPAPKVLVYSPPP | SEQ ID NO: 45 |
| PAPKVLVVSPPPLAP | SEQ ID NO: 46 |
| KVLVVSPPPLAPMPH | SEQ ID NO: 47 |
| VVSPPPLAPMPHPWF | SEQ ID NO: 48 |
| PPPLAPMPHPWFQLI | SEQ ID NO: 49 |
| LAPMPHPWFQLIFEG | SEQ ID NO: 50 |
| MPHPWFQLIFEGGEQ | SEQ ID NO: 51 |
| PWFQLIFEGGEQKTF | SEQ ID NO: 52 |
| QLIFEGGEQKTTELA | SEQ ID NO: 53 |
| FEGGEQKTTELARVY | SEQ ID NO: 54 |
| GEQKTTELARVYSAL | SEQ ID NO: 55 |
| KTTELARVYSALASF | SEQ ID NO: 56 |
| ELARVYSALASFMKV | SEQ ID NO: 57 |
| RVYSALASFMXVPFF | SEQ ID NO: 58 |
| SALASFMKVPFFDAG | SEQ ID NO: 59 |
| ASFMKVPFFDAGSVI | SEQ ID NO: 60 |
| MKVPFFDAGSVISTD | SEQ ID NO: 61 |
| PFFDAGSVISTDGVD | SEQ ID NO: 62 |
| DAGSVISTDGVDGIH | SEQ ID NO: 63 |
| SVISTDGVDGIHFTE | SEQ ID NO: 64 |
| STDGVDGIHFTEANN | SEQ ID NO: 65 |
| GVDGIHFTEANNRDL | SEQ ID NO: 66 |
| GIHFTEANNRDLGVA | SEQ ID NO: 67 |
| FTEANNRDLGVALAE | SEQ ID NO: 68 |
| ANNRDLGVALAEQVR | SEQ ID NO: 69 |
| RDLGVALAEQVRSLL | SEQ ID NO: 70 |

Peptide antigen was prepared as a 2 mg/ml stock solution in DMSO. First, 0.5 microliters of the stock solution were placed in each well of the 96 well plate in which the differentiated dendritic cells were previously placed. Then, 100 microliters of the diluted CD4+ T-cell solution as prepared above, were added to each well. Useful controls include diluted DMSO blanks, and tetanus toxoid positive controls.

The final concentrations in each well, at 20 microliter total volume are as follows:
$2 \times 10^4$ CD4+
$2 \times 10^5$ dendritic cells (R:S of 10:1)
5 µM peptide

EXAMPLE 3

I-MUNE® Assay for the Identification of Peptide T-Cell Epitopes in Perhydrolase Using Human T-Cells Once the assay reagents (i.e., cells, peptides, etc.) were prepared and distributed into the 96-well plates, the I-MUNE® assays were conducted. Controls included dendritic cells plus CD4+ T-cells alone (with DMSO carrier) and with tetanus toxoid (Wyeth-Ayerst), at approximately 5 Lf/mL.

Cultures were incubated at 37° C. in 5% $CO_2$ for 5 days. Tritiated thymidine (NEN) was added at 0.5 microCi/well. The cultures were harvested and assessed for incorporation the next day, using the Wallac TriBeta scintillation detection system (Wallace Oy).

All tests were performed at least in duplicate. All tests reported displayed robust positive control responses to the antigen tetanus toxoid. Responses were averaged within each experiment, then normalized to the baseline response. A positive event (i.e., a proliferative response) was recorded if the response was at least 2.95 times the baseline response.

The immunogenic responses (i.e., T-cell proliferation) to the prepared peptides from perhydrolase were determined. A relatively high overall background rate of responses to this peptide set was observed (5.35±3.41%) for the donors tested, as compared to an average of 3.15% for 11 other industrial proteins, indicating that humans are pre-exposed to the perhydrolase. Using these methods, one peptide of interest was identified, namely the peptide QLIFEGGEQKTTELA (SEQ ID NO:53). However, the structure value obtained for the protein indicates that it is comparatively non-immunogenic, as compared to other industrial proteins, including enzymes used in detergents. Nonetheless, as further described herein, it is contemplated that amino acid modifications in or around these peptides will provide variant perhydrolases suitable for use as even more hypo-allergenic/immunogenic perhydrolases. Indeed, it is contemplated that amino acid modifications in the range of the about 21 amino acids on either side of SEQ ID NO:53 will find use in the present invention, alone or in combination with changes in the sequence of SEQ ID NO:53, itself.

EXAMPLE 4

HLA Association with Epitope Peptides

The HLA-DR and DQ expression of donors tested in both rounds of assay testing described above are assessed using a commercially available PCR-based HLA typing kit (Bio-Synthesis). The phenotypic frequencies of individual HLA Class II DRB1 and DQB1 antigens among responders and non-responders to epitopes of interest are tested using a chi-squared analysis with 1 degree of freedom.

The phenotypic frequencies (presence or absence) of individual DR and DQ antigens among epitope reactive and non-reactive donors are tested using both a chi-square test (1 degree of freedom) and a Fisher's exact test. Wherever the HLA antigen is present in both reactive and non-reactive donors a relative risk (i.e., the increased or decreased likelihood of presenting a reaction conditioned on the presence of the HLA antigen) is computed. Allele frequencies among donors stratified by their reaction to the specific epitopes are also computed. In order to assess if the stimulation index differed between genotypes one-factor analyses of variance (ANOVA) are carried out using S-Plus 6 (Insightful).

Highly significant associations with both response and quantitative proliferative response to SEQ ID NO:53 and HLA antigen(s) of interest are identified.

Thus, the magnitude of the proliferative response to an individual peptide in responders and non-responders expressing epitope-associated HLA alleles are analyzed. An "individual responder to the peptide" is defined by a stimulation index of greater than 2.95. It is contemplated that the proliferative response in donors who express an epitope associated with HLA alleles are higher than in peptide responders who do not express the associated allele.

From the above, it is clear that the present invention provides methods and compositions for the identification of T-cell epitopes in wild-type perhydrolase. Once antigenic epitopes are identified, the epitopes are modified as desired, and the peptide sequences of the modified epitopes incorporated into a wild-type perhydrolase, so that the modified sequence is no longer capable of initiating the CD4$^+$ T-cell response or wherein the CD4$^+$ T-cell response is significantly reduced in comparison to the wild-type parent. In particular, the present invention provides means, including methods and compositions suitable for reducing the immunogenicity of perhydrolase.

EXAMPLE 5

Critical Residue Testing

In this Example, critical residue testing experiments for variants of peptides #75-76, #15, and #65 are described. In these experiments, alanine scans are performed for each peptide in order to produce variants of each of the parent peptides (i.e., peptides #15, #75-76 and #65). These variant peptides are synthesized using the multi-pin synthesis technique known in the art (See e.g., Maeji et al., J. Immunol. Meth., 134:23-33 [1990]).

The assay is performed as described in Example 3, utilizing the variant peptides on a set of donor samples. Proliferative responses are collated, and the results analyzed.

EXAMPLE 6

Epitope Modifications

As indicated above, specific amino acid substitutions in various peptides of interest are tested in the I-MUNE® assay (see above) on an additional set of donors along with the alanine scan mutagenized peptides. These peptides are then tested as 15-mer peptides offset by 3 amino acids across the peptide sequence of perhydrolase that encompasses epitope with SEQ ID NO:53. These tests are performed in order to ensure that the amino acid variants did not introduce a de novo CD4+ T-cell epitope in another frame.

EXAMPLE 7

PBMC Proliferation Assay

In this Example, experiments conducted to assess the ability of perhydrolase and epitope-modified perhydrolase to stimulate PBMCs are described. All of the proteins are purified to approximately 2 mg/ml.

The blood samples used in these experiments are the same as described above (i.e., before Example 1). The PBMCs are separated using Lymphoprep, as known in the art. The PBMCs are washed in PBS and counted using a Cell Dyn® 3700 blood analyzer (Abbott). The cell numbers and differentials are recorded. The PBMCs are resuspesnded to $4 \times 10^6$ cells/ml, in a solution of heat-inactivated human AB serum, RPMI 1640, pen/strep, glutamine, and 2-ME. Then, 2 mls per well are plated into 24-well plates. Two wells are used as no-enzyme controls. Then, the unmodified perhydrolase and modified perhydrolases are added to the wells at concentrations of 10 ug/ml, 20 ug/ml, and 40 ug/ml. The plates are incubated at 37° C., in a 5% $CO_2$, humidified atmosphere for 6-7 days. On the day of harvest, the cells in each well are mixed and resuspended in the wells. Then, 8 aliquots of 100 ul from each well are transferred to a 96-well microtiter plate. To these wells, 0.25 uCi of tritiated thymidine are added. These plates are incubated for 6 hours, the cells harvested and counted. For analysis, the data for the eight replicates from each well are averaged. For the controls, the two wells are sampled to provide a total of 32 replicates. Each set of eight control wells are averaged, and the four average values used to calculate a CV for each donor. SI values are calculated by dividing the average for each set of eight wells for each sample by the average CPM for the control well. The data are analyzed by creating a dataset representing the highest SI value achieved for each donor and each enzyme.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which that are obvious to those skilled in molecular biology, immunology, formulations, and/or related fields are intended to be within the scope of the present invention.

I claim:

1. An perhydrolase variant derived from a parent perhydrolase, wherein the perhydrolase variant has an amino acid sequence that is at least 95% identical to SEQ ID NO: 2, and comprises modifications in two or more of an amino acid residue selected from the group consisting of residues 151, 152, 155, 156, 157, 158, 160, 161, 162, 163, 164 and 165 of the perhydrolase of SEQ ID NO: 2.

2. A composition comprising the perhydrolase variant set forth in claim 1.

3. A detergent composition comprising the perhydrolase variant set forth in claim 1.

* * * * *